US012329745B2

(12) United States Patent
Katz

(10) Patent No.: US 12,329,745 B2
(45) Date of Patent: Jun. 17, 2025

(54) METHODS AND COMPOSITIONS FOR TREATING GLUCOCORTICOID EXCESS

(71) Applicant: Sparrow Pharmaceuticals, Inc., Portland, OR (US)

(72) Inventor: David A. Katz, Portland, OR (US)

(73) Assignee: Sparrow Pharmaceuticals, Inc., Portland, OR (US)

( * ) Notice: Subject to any disclaimer, the term of this patent is extended or adjusted under 35 U.S.C. 154(b) by 0 days.

(21) Appl. No.: 18/629,056

(22) Filed: Apr. 8, 2024

(65) Prior Publication Data

US 2024/0293375 A1 Sep. 5, 2024

Related U.S. Application Data

(60) Division of application No. 18/321,266, filed on May 22, 2023, now abandoned, which is a continuation of application No. PCT/US2023/067057, filed on May 16, 2023.

(60) Provisional application No. 63/364,759, filed on May 16, 2022.

(51) Int. Cl.
| A61P 5/46 | (2006.01) |
| A61K 9/00 | (2006.01) |
| A61K 31/4196 | (2006.01) |
| A61K 45/06 | (2006.01) |
| A61P 3/10 | (2006.01) |
| A61P 5/44 | (2006.01) |

(52) U.S. Cl.
CPC ........ *A61K 31/4196* (2013.01); *A61K 9/0053* (2013.01); *A61K 45/06* (2013.01); *A61P 5/44* (2018.01)

(58) Field of Classification Search
CPC .......... A61K 31/4196; A61P 5/44; A61P 5/46; A61P 35/00; A61P 3/10
See application file for complete search history.

(56) References Cited

U.S. PATENT DOCUMENTS

| 3,907,821 | A | 9/1975 | Gall |
| 4,577,020 | A | 3/1986 | Gall |
| 5,045,556 | A | 9/1991 | Allgeier |
| 5,098,922 | A | 3/1992 | Allgeier |
| 7,737,137 | B2 | 6/2010 | Brune |
| 8,377,923 | B2 | 2/2013 | Yoshimura |
| 8,871,208 | B2 | 10/2014 | Jacobson |
| 9,765,040 | B2 | 9/2017 | Kiso |
| 10,648,506 | B2 | 5/2020 | Mendoza |
| 10,894,054 | B2 | 1/2021 | Pruzanski |
| 12,220,412 | B2 | 2/2025 | Katz |
| 2004/0067222 | A1 | 4/2004 | Walker |
| 2004/0133011 | A1 | 7/2004 | Waddell |
| 2005/0277647 | A1 | 12/2005 | Link |
| 2006/0094699 | A1 | 5/2006 | Kampen |
| 2007/0224298 | A1 | 9/2007 | Talbott |
| 2007/0259854 | A1 | 11/2007 | Murakami |
| 2009/0082367 | A1 | 3/2009 | Yoshimura |
| 2011/0159005 | A1 | 6/2011 | Jacobson |
| 2013/0022677 | A1 | 1/2013 | Mullen |
| 2013/0338169 | A1 | 12/2013 | Bitner |
| 2017/0327474 | A1 | 11/2017 | Kiso |
| 2018/0010635 | A1 | 1/2018 | Mendoza |
| 2021/0137912 | A1 | 5/2021 | Tiganescu |
| 2021/0393622 | A1 | 12/2021 | Katz |
| 2023/0364060 | A1 | 11/2023 | Katz |

FOREIGN PATENT DOCUMENTS

| CA | 2580409 | 3/2006 |
| CN | 1909902 | 2/2007 |
| CN | 101014578 | 8/2007 |
| CN | 101198605 A | 6/2008 |
| EP | 1790641 | 5/2007 |
| EP | 1798226 | 6/2007 |
| EP | 1995243 | 11/2008 |
| EP | 2298747 | 3/2011 |
| JP | 2005170939 | 6/2005 |
| JP | 2007515484 | 6/2007 |
| TW | 201006804 | 2/2010 |
| WO | 2002076435 | 10/2002 |
| WO | 2003040110 | 5/2003 |
| WO | 2003059267 | 7/2003 |
| WO | 2003065983 | 8/2003 |
| WO | 2003104207 | 12/2003 |
| WO | 2003104208 | 12/2003 |
| WO | 2004014881 | 2/2004 |
| WO | 2004089367 | 10/2004 |
| WO | 2004089380 | 10/2004 |
| WO | 2004089470 | 10/2004 |
| WO | 2004106294 | 12/2004 |
| WO | 2005044192 | 5/2005 |

(Continued)

OTHER PUBLICATIONS

AANS ("Cushing's Syndrome/Disease." American Association of Neurological Surgeons (Apr. 2021) https://web.archive.org/web/20240529214944/https://www.aans.org/en/Patients/Neurosurgical-Conditions-and-Treatments/Cushings-Disease). (Year: 2021).*
Oda et al. (The Journal of Clinical Endocrinology & Metabolism, vol. 106, Issue 10, Oct. 2021, pp. e3865-e3880, https://doi.org/10.1210/clinem/dgab450). (Year: 2021).*
Katz et al. (Annals of the Rheumatic Diseases. vol. 82, Supplement 1, Jun. 2023, p. 208). (Year: 2023).*
Allende, F. et al., "LC-MS/MS Method for the Simultaneous Determination of Free Urinary Steroids", Chromatographia, 77(7-8):637-642, (2014).
An, G. et al., "Population Pharmacokinetics of the 11β-hydroxysteroid Dehydrogenase Type 1 Inhibitor ABT-384 in Healthy Volunteers Following Single and Multiple Dose Regimens", Biopharm Drug Dispos., 35(7):417-429, (2014).

(Continued)

*Primary Examiner* — James H Alstrum-Acevedo
*Assistant Examiner* — Chris E Simmons
(74) *Attorney, Agent, or Firm* — Cooley LLP

(57) ABSTRACT

The disclosure provides a method of treatment for glucocorticoid excess in a patient in need thereof, comprising administering to the patient a pseudo-irreversible HSD-1 inhibitor.

15 Claims, 14 Drawing Sheets

(56) References Cited

FOREIGN PATENT DOCUMENTS

| | | |
|---|---|---|
| WO | 2005060963 | 7/2005 |
| WO | 2005065683 | 7/2005 |
| WO | 2005097759 | 10/2005 |
| WO | 2006013948 | 2/2006 |
| WO | 2006030805 | 3/2006 |
| WO | 2006048750 | 5/2006 |
| WO | 2006068199 | 6/2006 |
| WO | 2006080533 | 8/2006 |
| WO | 2006134467 | 12/2006 |
| WO | 2006134481 | 12/2006 |
| WO | 2007007688 | 1/2007 |
| WO | 2007021941 | 2/2007 |
| WO | 2007040982 | 4/2007 |
| WO | 2007105753 | 9/2007 |
| WO | 2010001946 | 1/2010 |
| WO | 2010121814 | 10/2010 |
| WO | 2011068927 | 6/2011 |
| WO | 2012033070 | 3/2012 |
| WO | 2018117063 | 6/2018 |
| WO | 2020106337 | 5/2020 |
| WO | WO-2020106337 A1 * 5/2020 ......... A61K 31/4196 |  |
| WO | 2021180643 | 9/2021 |
| WO | 2023225507 | 11/2023 |

OTHER PUBLICATIONS

Carroll, B. et al., "A Specific Laboratory Test for the Diagnosis of Melancholia", Arch Gen Psychiatry, 38(1):15-22, (1981).

CN Patent Application No. 200980125940.0; Office Action, dated Jul. 17, 2012; 6 pages.

Csernansky, J. et al., "Plasma Cortisol and Progression of Dementia in Subjects with Alzheimer-Type Dementia", Am J Psychiatry, 163(12):2164-2169, (2006).

Davani, B. et al., "Type 1 11β-hydroxysteroid Dehydrogenase Mediates Glucocorticoid Activation and Insulin Release in Pancreatic Islets", J Biol Chem., 275(45):34841-34844, (2000).

EP Patent Application No. 05783391.5; Extended European Search Report, dated Jul. 24, 2009; 9 pages.

EP Patent Application No. 07738519.3; Extended European Search Report, dated Jun. 24, 2009; 6 pages.

EP Patent Application No. 09773524.5; Extended European Search Report, dated May 15, 2012; pages.

Erhardt, A. et al., "Regulation of the Hypothalamic-Pituitary-Adrenocortical System in Patients with Panic Disorder", Neuropsychopharmacology, 31(11):2515-2522, (2006).

Erkut, Z. et al., "Stress of Dying is not Suppressed by High-dose Morphine or by Dementia", Neuropsychopharmacology, 29(1):152-157, (2004).

Holman, A. et al., "A Randomized, Double-Blind, Placebo-Controlled Trial of Pramipexole, a Dopamine Agonist, in Patients with Fibromyalgia Receiving Concomitant Medications", Arthritis & Rheumatism, 52(8):2495-2505, (2005).

Hong, H. et al., "Hypothalamic-Pituitary-Adrenal Reactivity in Boys with Attention Deficit Hyperactivity Disorder", Yonsei Med J., 44(4):608-614, (2003).

International Application No. PCT/JP2009/062081; International Preliminary Report on Patentability, date of issuance Jan. 5, 2011; 07 pages.

International Application No. PCT/JP2009/062081; International Search Report and Written Opinion of the International Searching Authority, date of mailing Sep. 1, 2009; 11 pages.

International Application No. PCT/JP2011/070205; International Search and Written Opinion of the International Searching Authority (English translation), date of mailing Nov. 15, 2011; 9 pages.

International Application No. PCT/US2019/046449; International Preliminary Report on Patentability, date of issuance Jun. 3, 2021; 7 pages.

International Application No. PCT/US2019/046449; International Search Report and Written Opinion of the International Searching Authority, date of mailing Oct. 24, 2019; 9 pages.

International Application No. PCT/US2023/067057; International Search Report and Written Opinion of the International Searching Authority, date of mailing Oct. 11, 2023; 13 pages.

Katritzky, A. et al., "Ring and Side Chain Reactivities of 1-([1,3,4]oxadiazol-2-ylmethyl)-1 H-benzotriazole", ARKIVOC (ii), pp. 101-108, (2001).

Katz, D. et al., "Peripheral and Central Nervous System Inhibition of 11β-hydroxysteroid Dehydrogenase Type 1 in Man by the Novel Inhibitor ABT-384", Transl Psychiatry, 3(8):e295, 7 pages, (2013).

Kiso, T. et al., "Analgesic Effects of ASP3662, a Novel 11β-hydroxysteroid Dehydrogenase 1 Inhibitor, in Rat Models of Neuropathic and Dysfunctional Pain", Br J Pharmacol., 175(19):3784-3796, (2018).

Lindsay, R. et al., "Subcutaneous Adipose 11β-hydroxysteroid Dehydrogenase Type 1 Activity and Messenger Ribonucleic Acid Levels are Associated with Adiposity and Insulinemia in Pima Indians and Caucasians", J Clin Endocrinol Metab., 88(6):2738-2744, (2003).

Masuzaki, H. et al., "A Transgenic Model of Visceral Obesity and the Metabolic Syndrome", Science, 294:2166-2170, (2001).

Masuzaki, H. et al., "Transgenic Amplification of Glucocorticoid Action in Adipose Tissue Causes High Blood Pressure in Mice", J Clin Invest., 112(1):83-90, (2003).

Mease, P. et al.,"A Randomized, Double-Blind, Placebo-Controlled, Phase III Trial of Pregabalin in the Treatment of Patients with Fibromyalgia", J Rheumatol, 35(3):502-514, (2008).

Morton, N. et al., "Improved Lipid and Lipoprotein Profile, Hepatic Insulin Sensitivity, and Glucose Tolerance in 11β-Hydroxysteroid Dehydrogenase Type 1 Null Mice", J Biol Chem., 276(44):41293-41300, (2001).

Pappagallo, M. "Newer Antiepileptic Drugs: Possible Uses in the Treatment of Neuropathic Pain and Migraine", Clinical Therapeutics, 25(10):2506-2538, (2003).

Patani, G. et al., "Bioisosterism: A Rational Approach in Drug Design", Chem Rev., 96(8):3147-3176, (1996).

Rask, E. et al., "Tissue-Specific Dysregulation of Cortisol Metabolism in Human Obesity", J Clin Endocrinol Metab., 86(3):1418-1421, (2001).

Rauz, S. et al., "Expression and Putative Role of 11β-Hydroxysteroid Dehydrogenase Isozymes within the Human Eye", Invest Ophthalmol Vis Sci., 42(9):2037-2042, (2001).

Russell, I. et al., "Efficacy and Safety of Duloxetine for Treatment of Fibromyalgia in Patients with or without Major Depressive Disorder: Results from a 6-month, Randomized, Double-blind, Placebo-controlled, Fixed-dose Trial", Pain, 136(3):432-444, (2008).

Sandeep, T. et al., "11β-Hydroxysteroid Dehydrogenase Inhibition Improves Cognitive Function in Healthy Elderly Men and Type 2 Diabetics", PNAS, 101(17):6734-6739, (2004).

Sindrup, S. et al., "Antidepressants in the Treatment of Neuropathic Pain", Basic & Clinical Pharmacology & Toxicology, 96(6):399-409, (2005).

Skaer, T. "Fibromyalgia: Disease Synopsis, Medication Cost Effectiveness and Economic Burden", PharmacoEconomics, 32:457-466, (2014).

U.S. Appl. No. 15/664,733; Final Office Action dated Oct. 11, 2018; 18 pages.

U.S. Appl. No. 11/663,089; Non-Final Office Action, dated Apr. 16, 2009; 14 pages.

U.S. Appl. No. 11/663,089; Notice of Allowance, dated Apr. 6, 2010; 8 pages.

U.S. Appl. No. 12/293,214; Non-Final Office Action, dated Nov. 23, 2009; 15 pages.

U.S. Appl. No. 18/321,266; Final Office Action dated May 22, 2024; pages.

Veen, G. et al., "Salivary Cortisol, Serum Lipids, and Adiposity in Patients with Depressive and Anxiety Disorders", Metabolism, 58(6):821-827, (2009).

Woolf, C. et al., "Neuropathic Pain: Aetiology, Symptoms, Mechanisms, and Management", Lancet, 353 (9168):1959-1964, (1999).

Yau, J. et al., "Lack of Tissue Glucocorticoid Reactivation in 11β-hydroxysteroid Dehydrogenase Type 1 Knockout Mice Ameliorates Age-Related Learning Impairments", PNAS, 98(8):4716-4721, (2001).

(56) References Cited

OTHER PUBLICATIONS

Wolfe, F. et al., "The American College of Rheumatology 1990 Criteria for the Classification of Fibromyalgia", Arthritis and Rheumatism, 33(2):160-172, (1990).
Zhang, X. et al., "Cortisol and Cytokines in Chronic and Treatment-Resistant Patients with Schizophrenia: Association with Psychopathology and Response to Antipsychotics", Neuropsychopharmacology, 30(8):1532-1538, (2005).
Aresta et al., "When to Suspect Hidden Hypercortisolism in Type 2 Diabetes: A Meta-Analysis" Endocrine Practice, 27, 2021, pp. 1216-1224.
Bancos et al., "Urine steroid metabolomics for the differential diagnosis of adrenal incidentalomas in the EURINE-ACT study: a prospective test validation study" Lancet Diabetes Endocrinol, 2020, Jul. 23, 2020, 9 pages, with Supplementary Appendix, 39 pages.
Basu et al., "Liver Is the Site of Splanchnic Cortisol Production in Obese Nondiabetic Humans" Diabetes, Jan. 2009, vol. 58, 7 pages.
Bellaire et al., "Safety, Pharmacokinetics, and Pharmacodynamics of ASP3662, a Novel 11β-Hydroxysteroid Dehydrogenase Type 1 Inhibitor, in Healthy Young and Elderly Subjects" Clin Transl Sci, 2019, 12, pp. 291-301.
Bianzano et al., "Safety, tolerability, pharmacodynamics and pharmacokinetics following once-daily doses of BI 187004, an inhibitor of 11 beta-hydroxysteroid dehydrogenase-1, over 28 days in patients with type 2 diabetes mellitus and overweight or obesity" Diabetes Obes Metab., 2022, pp. 1-12.
Bianzano et al., "Selective Inhibition of 11 beta-Hydroxysteroid-dehydrogenase-1 with BI 187004 in Patients with Type 2 Diabetes and Overweight or Obesity: Safety, Pharmacokinetics, and Pharmacodynamics After Multiple Dosing Over 14 Days" Exp Clin Endocrinol Diabetes, 2022, 130, pp. 773-782.
Catargi et al., "Occult Cushing's Syndrome in Type-2 Diabetes" The Journal of Clinical Endocrinology & Metabolism, Dec. 2003, 88(12), pp. 5808-5813.
Constantinopoulos et al., "Cortisol in tissue and systemic level as a contributing factor to the development of metabolic syndrome in severely obese patients" European Journal of Endocrinology, 2015, 172, pp. 69-78.
Co-pending U.S. Appl. No. 18/980,242, filed Dec. 13, 2024, David A. Katz.
Curriculum Vitae, David Aaron Katz, Ph.D., 8 pages.
Defronzo et al., "Study protocol for a prospective, multicentre study of hypercortisolism in patients with difficult-to-control type 2 diabetes (Catalyst): prevalence and treatment with mifepristone" BMJ Open, 2024, 12 pages.
Delivanis et al., "Modern Management of Mild Autonomous Cortisol Secretion" Clinical Pharmacology & Therapeutics, Dec. 2019, vol. 106, No. 6, 13 pages.
Dodd et al., "Effect of Glucocorticoid and 11β-Hydroxysteroid-Dehydrogenase Type 1 (11β-HSD1) in Neurological and Psychiatric Disorders" International Journal of Neuropsychopharmacology, 2022, 25(5), pp. 387-398.
Dube et al., "11β-Hydroxysteroid Dehydrogenase Types 1 and 2 Activity in Subcutaneous Adipose Tissue in Humans: Implications in Obesity and Diabetes" J Clin Endocrinol Metab, Jan. 2015, 100(1): E70-E76, 13 pages.
Dube et al., "Hepatic 11β-hydroxysteroid dehydrogenase type 1 activity in obesity and type 2 diabetes using a novel triple tracer cortisol technique" Diabetologia, Jul. 2014, 57(7): 1446-1455, 22 pages.
Feig et al., "Effects of an 11β-hydroxysteroid dehydrogenase type 1 inhibitor, MK-0916, in patients with type 2 diabetes mellitus and metabolic syndrome" Diabetes, Obesity and Metabolism, Jun. 2011, vol. 13, No. 6, pp. 498-504.
Findling et al., "Differentiation of pathologic/neoplastic hypercortisolism (Cushing's syndrome) from physiologic/non-neoplastic hypercortisolism (formerly known as pseudo-Cushing's syndrome)" European Journal of Endocrinology, 2017, 176, R205-R216.

Fleseriu et al., "A double-blind, randomized, placebo-controlled trial of SPI-62 safety and efficacy for the treatment of Cushing's syndrome" Endocrine Abstracts, 2021, 73, AEP546, 4 pages.
Freude et al., "Safety, pharmacokinetics and pharmacodynamics of BI 135585, a selective 11β-hydroxysteroid dehydrogenase-1 (HSD1) inhibitor in humans: liver and adipose tissue 11β-HSD1 inhibition after acute and multiple administrations over 2 weeks" Diabetes, Obesity and Metabolism, May 2016, vol. 18, No. 5, pp. 483-490.
Gutierrez et al., "Continuous inhibition of 11β-hydroxysteroid dehydrogenase type I in adipose tissue leads to tachyphylaxis in humans and rats but not in mice" British Journal of Pharmacology, 2015, 172, pp. 4806-4816.
Heise et al., "Safety, efficacy and weight effect of two 11β-HSD1 inhibitors in metformin-treated patients with type 2 diabetes" Diabetes, Obesity and Metabolism, Nov. 2014, vol. 16, No. 11, pp. 1070-1077.
Hosfield et al., "Conformational Flexibility in Crystal Structures of Human 11β-Hydroxysteroid Dehydrogenase Type I Provide Insights into Glucocorticoid Interconversion and Enzyme Regulation" The Journal of Biological Chemistry, vol. 280, No. 6, Issue of Feb. 11, 2005, pp. 4639-4648.
Li et al., "Discovery of Clinical Candidate BMS-823778 as an Inhibitor of Human 11B- Hydroxysteroid Dehydrogenase Type 1 (11β-HSD-1)" ACS Med. Chem. Lett., 2018, 9, pp. 1170-1174, with Supporting Information, 18 pages.
Ling et al., "Mechanistic Insight on the Mode of Action of Colletoic Acid" J Med Chem., Aug. 8, 2019; 62(15), pp. 6925-6940, 38 pages.
Markey et al., "11β-Hydroxysteroid Dehydrogenase Type 1 inhibition in Idiopathic Intracranial Hypertension: a double-blind randomized controlled trial" Brain Communications, Aug. 25, 2020, 2(2), 12 pages.
Morgan et al., "11β-HSD1 is the major regulator of the tissue-specific effects of circulating glucocorticoid excess" PNAS, Jun. 2, 2014, E2482-E2491, with Supporting Information, 10 pages, www.pnas.org/cgi/content/short/1323681111.
Mostefaoui et al., "Virtual Screening of Triazoles Inhibitors of 11B Hydroxysteroid Dehydrogenase Enzymes Using Adme Molecular Docking, and Molecular Dynamics Simulation Studies" Journal of Fundamental and Applied Sciences, May 1, 2020, 16 pages.
NCT02372578, Painful Diabetic Peripheral Neuropathy, Astellas, ISN 3662-CL-0049, 2016, 25 pages.
NCT02372578, Sponsor: Astellas, Study No. 3662-CL-0049, Sep. 2018, 5 pages.
Non-Final Office Action for U.S. Appl. No. 18/321,266 mailed Feb. 15, 2024, 12 pages.
Oda et al., "An open-label phase I/IIa clinical trial of 11β-HSD1 inhibitor for Cushing's syndrome and autonomous cortisol secretion" (The Journal of Clinical Endocrinology & Metabolism, vol. 106, Issue 10, Oct. 2021, pp. e3865-e3880, https://doi.org/10.1210/clinem/dgab450). (Year: 2021), Supplementary Materials, 15 pages.
Patel et al., "Discovery of adamantane ethers as inhibitors of 11β-HSD-1: Synthesis and biological evaluation" Bioorganic & Medicinal Chemistry Letters, 2007, 17, pp. 750-755.
Restriction Requirement for U.S. Appl. No. 18/321,266 mailed Oct. 11, 2023, 8 pages.
Rosenstock et al., "The 11-β-Hydroxysteroid Dehydrogenase Type 1 Inhibitor INCB13739 Improves Hyperglycemia in Patients With Type 2 Diabetes Inadequately Controlled by Metformin Monotherapy" Diabetes Care, Jul. 2018, vol. 33, No. 7, pp. 1516-1522, with Supplemental Information, 7 pages.
Scaroni et al., "Glucose Metabolism Abnormalities in Cushing Syndrome: From Molecular Basis to Clinical Management" Endocrine Reviews, 2017, 38, pp. 189-219.
Scott et al., "Discovery of a Potent, Selective, and Orally Bioavailable Acidic 11β-Hydroxysteroid Dehydrogenase Type 1 (11β-HSD1) Inhibitor: Discovery of 2-[(3S)-1-[5-(Cyclohexylcarbamoyl)-6-propylsulfanylpyridin-2-yl]-3-piperidyl]acetic Acid (AZD4017)" J. Med. Chem., 2012, 55, pp. 5951-5964.
Sharma et al., "Cushing's syndrome: epidemiology and developments in disease management" Clinical Epidemiology, 2015, 7, pp. 281-293.

(56) References Cited

OTHER PUBLICATIONS

Sorensen et al., "Adamantane 11-β-HSD-1 inhibitors: Application of an isocyanide multicomponent reaction" Bioorganic & Medicinal Chemistry Letters, 2006, 16, pp. 5958-5962.

Stewart et al., "Selective Inhibitors of 11β-Hydroxysteroid Dehydrogenase Type 1 for Patients With Metabolic Syndrome" Diabetes, vol. 58, Jan. 2009, 2 pages.

Stimson et al., "Cortisol Release From Adipose Tissue by 11β-Hydroxysteroid Dehydrogenase Type 1 in Humans" Diabetes, Jan. 2009, vol. 58, 8 pages.

Sun et al., "Discovery and Initial SAR of Arylsulfonylpiperazine Inhibitors of 11β-Hydroxysteroid Dehydrogenase Type 1 (11β-HSD1)" Bioorganic & Medicinal Chemistry Letters, 2008, 18, pp. 3513-3516.

Terzolo et al., "Screening of Cushing's Syndrome in Outpatients with Type 2 Diabetes: Results of a Prospective Multicentric Study in Italy" J Clin Endocrinol Metab, Oct. 2012, 97(10), pp. 3467-3475.

Thomas et al., "Crystal structures of 11β-hydroxysteroid dehydrogenase type 1 and their use in drug discovery" Future Med Chem., Mar. 2011; 3(3), pp. 367-390, 53 pages.

Tomlinson et al., "11β-Hydroxysteroid Dehydrogenase Type 1: A Tissue-Specific Regulator of Glucocorticoid Response" Endocrine Reviews, Oct. 2004, 25(5), pp. 831-866.

Valsamakis et al., "11β-Hydroxysteroid Dehydrogenase Type 1 Activity in Lean and Obese Males with Type 2 Diabetes Mellitus" J Clin Endocrinol Metab, Sep. 2004, 89(9), pp. 4755-4761.

Venier et al., "Discovery of SAR184841, a potent and long-lasting inhibitor of 11β-hydroxysteroid dehydrogenase type 1, active in a physiopathological animal model of T2D" Bioorganic & Medicinal Chemistry Letters, 2013, 23, pp. 2414-2421.

Wu et al., "Population Target-Mediated Pharmacokinetic/Pharmacodynamic Modeling to Evaluate SPI-62 Exposure and Hepatic 11β-Hydroxysteroid Dehydrogenase Type 1 (HSD-1) Inhibition in Healthy Adults" Clinical Pharmacokinetics, Jul. 15, 2023, 14 pages.

\* cited by examiner

AS2570469

METHODS AND COMPOSITIONS FOR TREATING GLUCOCORTICOID EXCESS

This application is divisional of U.S. application Ser. No. 18/321,266, filed May 22, 2023, which is a bypass continuation of International Application No. PCT/US2023/067057, filed May 16, 2023, which claims the benefit of priority of U.S. Provisional Application No. 63/364,759, filed May 16, 2022, the disclosures of each are hereby incorporated by reference as if written herein in their entireties.

Glucocorticoids (GCs) are corticosteroids that bind to the glucocorticoid receptor (GR), which is present in many cell types in the human body. In addition, GCs also bind to the mineralocorticoid receptor (MR) and non-genomic receptors. GCs are involved in cardiovascular, metabolic, immunologic, osteal, muscular, dermatological, ocular, psychiatric, cognitive, circadian, and homeostatic functions. GC excess in humans can lead to myriad symptoms and illnesses.

GCs can be endogenous (natural) or synthetic. Cortisol is an important endogenous glucocorticoid. Natural GCs include others that are active (e.g., corticosterone) as well as those that are considered inactive (e.g., cortisone) as they don't activate GR or MR. Synthetic glucocorticoids include prednisone, prednisolone, methylprednisolone, dexamethasone, among many others, as well as derivatives of these. Both cortisol (as a medication, typically known as hydrocortisone) and synthetic GCs are used as medications to treat autoimmune diseases and other conditions.

There are three predominant known forms of GC excess in human. (1) Excess of the natural GC cortisol due to an ACTH- or CRH-secreting tumor, including Cushing's disease (pituitary adenoma), ectopic ACTH secretion, and ectopic CRH secretion. (2) Excess of cortisol due to a cortisol-secreting tumor, including autonomous cortisol secretion [ACS; also known as mild autonomous cortisol secretion (MACS) or mildautonomous cortisol excess (MACE)] and adrenal Cushing's syndrome. (3) Excess of hydrocortisone or a synthetic GC during administration for treatment of an autoimmune or other disorder, or to prevent transplanted organ rejection.

HSD-1 is an intracellular enzyme that converts GCs from inactive (e.g., cortisone, prednisone) to active (e.g., cortisol, prednisolone) form. It is a major source of intracellular cortisol and thought to be a major source of intracellular synthetic GC, in many cell types. Excess intracellular GC activates GR and MR, along with non-genomic receptors, resulting in the tissue-specific morbidity observed in subjects with GC excess. HSD-1 inhibition may therefore ameliorate those symptoms. The present disclosure describes an important type of HSD-1 inhibitors, pseudo-irreversible HSD-1 inhibitors.

Provided is a method of treatment for glucocorticoid excess in a patient in need thereof, comprising administering to the patient a pseudo-irreversible HSD-1 inhibitor.

Also provided is a method for improvement or prevention or reversal of symptoms of glucocorticoid excess in a patient in need thereof, comprising administering to the patient a pseudo-irreversible HSD-1 inhibitor.

Also provided is a method of reducing the levels of urinary tetrahydrocortisols in a patient having glucocorticoid excess, comprising administering to the patient a pseudo-irreversible HSD-1 inhibitor, wherein the levels of said urinary tetrahydrocortisols are elevated compared to an asymptomatic patient.

These and other aspects of the invention will be apparent upon reference to the following detailed description. To this end, various references are set forth herein which describe in more detail certain background information, procedures, compounds, and/or compositions, and are each hereby incorporated by reference in their entirety.

DETAILED DESCRIPTION OF THE DISCLOSURE

Overview

Figure 1:
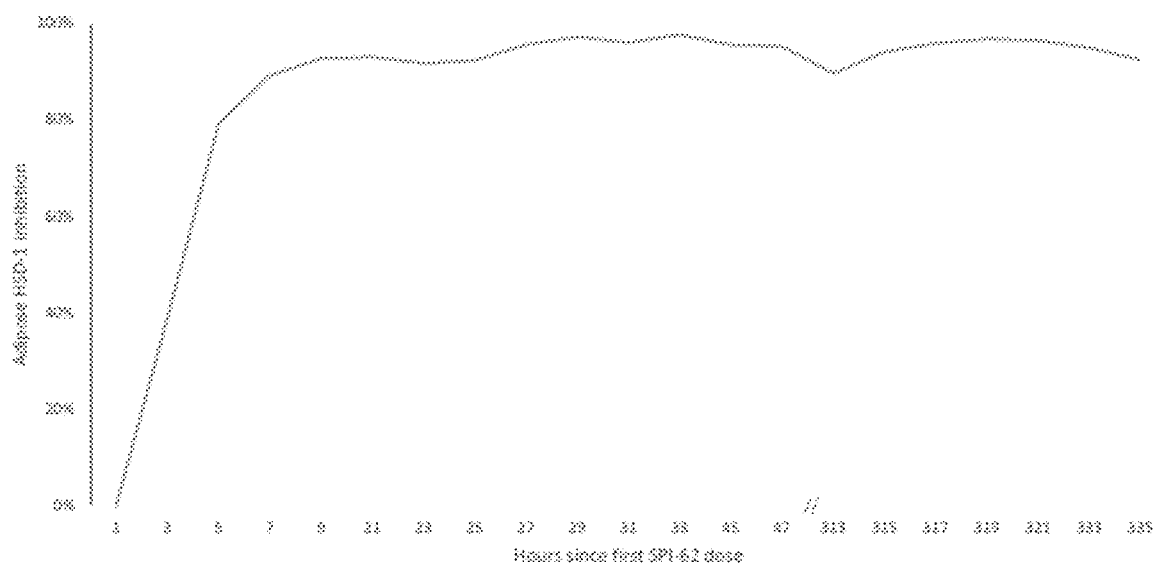
FIG. 1—Shows adipose HSD-1 inhibition by SPI-62. Adipose HSD-1 inhibition was detected between 2-4 hours after a single dose, reached maximal measurable levels during the $2^{nd}$ dose interval, and was almost identical during the $2^{nd}$ and $14^{th}$ dose intervals.

Provided is a method to treat a patient with glucocorticoid (GC) excess by administration of a pseudo-irreversible inhibitor of 11θ-hydroxysteroid dehydrogenase type 1 (HSD-1) to the patient. Also provided is a method to improve or prevent specific symptoms of a patient with GC excess by administration of a pseudo-irreversible HSD-1 inhibitor. Also provided is a method of reducing the levels of urinary tetrahydrocortisols in a patient having glucocorticoid excess, comprising administering to the patient a pseudo-irreversible HSD-1 inhibitor, wherein the levels of said urinary tetrahydrocortisols are elevated compared to an asymptomatic patient. Also provided is a method to treat, or improve specific symptoms of, a patient with GC excess by co-administration of a pseudo-irreversible HSD-1 inhibitor with a GC medication.

In some embodiments, glucocorticoid excess refers to a condition or physiological state in an individual in which the levels of urinary tetrahydrocortisols or other products of glucocorticoid breakdown, are elevated relative to a reference patient or sample, or relative to a patient not experiencing glucocorticoid excess. In some embodiments, the symptoms of glucocorticoid excess comprise cardiovascular, metabolic, immunologic, osteal, muscular, dermatological, ocular, psychiatric, cognitive, circadian, and homeostatic symptoms.

In some embodiments, the pseudo-irreversible HSD-1 inhibitor does not show tachyphylaxis for human adipose HSD-1 inhibition. In some embodiments, the HSD-1 inhibitor is selected from SPI-62 and BI-187004, or a pharmaceutically acceptable salt thereof. In some embodiments, the HSD-1 inhibitor is SPI-62, or a pharmaceutically acceptable salt thereof.

In some embodiments, the pseudo-irreversible HSD-1 inhibitor is characterized by human pharmacokinetics consistent with target-mediated drug disposition. In some embodiments, the pseudo-irreversible HSD-1 inhibitor is selected from SPI-62, ABT-384, MK-0736, MK-0916, BMS-823778, UE-2343, AMG-221, and BI-187004, or a pharmaceutically acceptable salt thereof.

In some embodiments, plasma exposures of the pseudo-irreversible HSD-1 inhibitor are less than dose-proportional after low single doses and dose-proportional after multiple low doses. In some embodiments, the doses are 10 mg or lower, or 6 mg or lower, or 4 mg or lower.

In some embodiments, the pseudo-irreversible HSD-1 inhibitor is characterized by human pharmacodynamics consistent with target-mediated drug-disposition. In some embodiments, the pharmacodynamic half-life of the HSD-1 inhibitor for hepatic HSD-1 inhibition is extended compared to its pharmacokinetic half-life. In some embodiments, the pseudo-irreversible HSD-1 inhibitor is characterized by a pharmacodynamic half-life for human hepatic HSD-1 inhibition of at least 1 week. In some embodiments, the pharmacodynamic half-life for human hepatic HSD-1 inhibition is at least 2 weeks. In some embodiments, the pharmacodynamic half-life for human hepatic HSD-1 inhibition is at least 4 weeks. In some embodiments, the pseudo-irreversible HSD-1 inhibitor is selected from SPI-62 and ABT-384, or a pharmaceutically acceptable salt thereof.

In some embodiments, the pseudo-irreversible HSD-1 inhibitor is characterized by fast-on, slow-off in vitro binding kinetics to human HSD-1. In some embodiments, the residence time of the HSD-1 inhibitor is at least about 500 seconds. In some embodiments, the pseudo-irreversible HSD-1 inhibitor is selected from SPI-62, ABT-384, KR-67607, UE-2343, and BI-187004, or a pharmaceutically acceptable salt thereof.

In some embodiments, the pseudo-irreversible HSD-1 inhibitor is characterized by apparent fast-on, slow-off in vivo binding kinetics to human HSD-1. In some embodiments, the model-estimated $k_{off}$ is less than 0.3 h$^{-1}$. In some embodiments, the model-estimated $k_{off}$ is less than 1.0 h$^{-1}$. In some embodiments, the model-estimated $k_{off}$ is less than 3.0 h$^{-1}$. In some embodiments, the pseudo-irreversible HSD-1 inhibitor is selected from SPI-62 and ABT-384, or a pharmaceutically acceptable salt thereof.

In some embodiments, the pseudo-irreversible HSD-1 inhibitor is characterized by having a greater potency in vivo than in vitro. In some embodiments, the model-estimated $K_d$ of the HSD-1 inhibitor is lower than that of the HSD-1 inhibitor $K_i$. In some embodiments, the model-estimated $K_d$ is at least 50-fold lower than $K_i$. In some embodiments, the model-estimated $K_d$ is at least 100-fold lower than that $K_i$. In some embodiments, the model-estimated $K_d$ is at least 200-fold lower than $K_i$. In some embodiments, the model-estimated adipose IC$_{50}$ of the HSD-1 inhibitor is lower than that of the HSD-1 inhibitor measured in vitro. In some embodiments, the model-estimated adipose IC$_{50}$ is at least 100-fold lower than that measured in vitro. In some embodiments, the model-estimated adipose IC$_{50}$ is at least 300-fold lower than that measured in vitro. In some embodiments, the model-estimated adipose IC$_{50}$ is at least 700-fold lower than that measured in vitro. In some embodiments the pseudo-irreversible inhibitor is SPI-62, or a pharmaceutically acceptable salt thereof.

In some embodiments, the pseudo-irreversible HSD-1 inhibitor forms hydrogen bonds to the pyrophosphate of NADPH in the human HSD-1 active site. In some embodiments, the pseudo-irreversible HSD-1 inhibitor is selected from SPI-62, ABT-384, KR-67607, SAR-184481, Compound A, and Compound B, or a pharmaceutically acceptable salt thereof.

In some embodiments, the pseudo-irreversible HSD-1 inhibitor forms an aromatic stacking interaction with NADPH in the human HSD-1 active site. In some embodiments, the pseudo-irreversible HSD-1 inhibitor is selected from BMS-823778, MK-0916, Compound C, and Compound D, or a pharmaceutically acceptable salt thereof.

Also provided is a method for improvement or prevention of symptoms of glucocorticoid excess in a patient in need thereof, comprising administering a brain penetrant pseudo-irreversible HSD-1 inhibitor to the patient. In one embodiment, the symptoms comprise psychiatric (e.g., mood), cognitive, or circadian (e.g., sleep) symptoms. In some embodiments, the psychiatric symptoms are chosen from depression, anxiety, hypomania, mania, and psychosis; or the cognitive symptoms are chosen from impairments in memory, visuospatial processing, reasoning, verbal learning, and language performance; or the circadian symptoms are chosen from insomnia, daytime fatigue, sleep apnea, fragmented sleep, increased nocturnal motor activity, and abnormal REM sleep.

In some embodiments, the methods described herein further comprise administration of a glucocorticoid medication to the patient. In some embodiments, the HSD-1 inhibitor is administered in a fixed-dose combination with the glucocorticoid medication. In some embodiments, the HSD-1 inhibitor and the glucocorticoid medication are co-packaged for separate administration. In some embodiments, the HSD-1 inhibitor is administered and packaged separately from the glucocorticoid medication. In some embodiments, the glucocorticoid medication is selected from prednisolone, methylprednisolone, dexamethasone, hydrocortisone, budesonide, deflazacort, beclomethasone, ciclesonide, fluticasone, mometasone, triamcinolone, flunisolide, clobetasol, betamethasone, fluocinonide, flurandrenolide, clocortolone, halobetasol, desoximetasone, desonide, halcinonide, prednicarbate, diflorasone, amcinonide, alclometasone, difluprednate, loteprednol, fluorometholone, rimexolone, and medrysone, or a pharmaceutically acceptable salt or ester derivative thereof.

In some embodiments, the patient has an ACTH- or CRH-secreting tumor. In some embodiments, the patient has a cortisol-secreting tumor.

In another embodiment, the pseudo-irreversible HSD-1 inhibitor is administered orally. In another embodiment, the pseudo-irreversible HSD-1 inhibitor is administered intravenously. In another embodiment, the pseudo-irreversible HSD-1 inhibitor is administered intramuscularly or subcutaneously. In another embodiment, the pseudo-irreversible HSD-1 inhibitor is administered by inhalation or intranasally. In another embodiment, the pseudo-irreversible HSD-1 inhibitor is administered ocularly. In another embodiment, the pseudo-irreversible HSD-1 inhibitor is administered topically.

The present disclosure describes an important type of HSD-1 inhibitors, pseudo-irreversible HSD-1 inhibitors, which have demonstrated a previously unknown advantage for two members of that sub-class, BI-187004 and SPI-62. Unlike certain other HSD-1 inhibitors (e.g., AZD4017, AZD8329, BI-135585), BI-187004 shows limited, and SPI-62 does not show, tachyphylaxis of human adipose HSD-1 inhibition with multiple dosing. As adipose HSD-1 regulates prominent cardiometabolic morbidities of GC excess, an inhibitor that does not lose adipose HSD-1 can be expected to be clinically superior to other HSD-1 inhibitors for treatment of GC excess. It was considered that durable human adipose HSD-1 inhibition is a shared characteristic of pseudo-irreversible inhibitors, which are defined as HSD-1 inhibitors that show one or more of the following four properties.

(1) Clinical pharmacokinetics consistent with target-mediated drug disposition (TMDD). Following a low single dose, a large fraction of the administered dose is quickly sequestered by the target and consequently only a small portion of drug molecules are in central circulation. As a result, the drug plasma concentrations are much lower than would be for a drug with linear kinetics. With a higher single dose, the low-capacity target is saturated quickly. The fraction of the dose sequestered by the target decreases inversely to dose. As a result, the drug appears to have linear pharmacokinetics at high single doses because the portion trapped by the target is minimal compared with the total dose. The striking nonlinear pharmacokinetics observed following the first low dose(s) turn into linear pharmacokinetics after repeated low doses.

(2) Clinical pharmacodynamics consistent with TMDD. Early following low doses, target engagement might be detected even before plasma levels are detectable. Across a wide dose range, target engagement may appear to be independent of concentration; high target engagement may be associated with low plasma levels. Pharmacological half-life can be quite extended as the drug remains bound to the target in the microenvironment even after plasma levels have declined below the limit of detection.

(3) Fast-on, slow-off binding to HSD-1, with an enzyme resident time ($k_d^{-1}$) longer that other HSD-1 inhibitors. This results in a dissociation constant ($k_{off}$) substantially lower than the association constant ($k_{on}$), which can be revealed via population PK modeling of clinical trial data. $K_d$, i.e., the ratio of $k_{off}$ to $k_{on}$, is substantially lower than the measured $K_i$. As a consequence of fast-on, slow-off binding, the concentration that results in 50% of maximum HSD-1 inhibition ($IC_{50}$) in vivo is substantially lower than the $IC_{50}$ measured in vitro, which can be revealed via population PK-PD modeling of clinical trial data.

(4) When bound to human HSD-1, forms a non-covalent ternary complex with the enzyme as well as the cofactor NADPH. That is a structural basis for slow-off binding and TMDD behaviors. The binding energy of both the inhibitor and NADPH must be overcome for inhibitor dissociation from the enzyme. The ternary complex is also resistant to competition by HSD-1 substrates, which is of particular importance in GC excess when circulating levels of a substrate are increased. In some embodiments, hydrogen bonding and aromatic stacking interaction are distinct modes by which HSD-1 inhibitors link or complex to NADPH in the active site.

Cortisol and Cortisone

Cortisol is a glucocorticoid hormone, produced and released by the adrenal glands. Less than 6% of circulating cortisol is bioavailable to tissues, as it is extensively bound to corticosteroid binding globulin and albumin. Circulating cortisone is substantially more bioavailable to tissues, as it has only 12% of cortisol's affinity for corticosteroid binding globulin. Elevated level of glucocorticoids can lead to insulin resistance by decreasing insulin-dependent glucose uptake, enhancing hepatic gluconeogenesis, and inhibiting insulin secretion from pancreatic cells. Patients with sustained glucocorticoid excess can develop dyslipidemia, visceral obesity, and other metabolic syndromes. Other physiological symptoms can include rapid weight gain, mainly in the face, chest, and abdomen, contrasted with slender arms and legs, flushed and round face, high blood pressure, osteoporosis, dermatological changes, e.g., bruises and purple stretch marks, muscle weakness, and mood swings, which present as anxiety, depression, or irritability, among others.

Cortisone levels have been observed to increase with pseudo-irreversible HSD-1 inhibitor administration. For example, liver cortisone levels increased substantially with both single and multiple doses of SPI-62, as evidenced by increases of the excreted cortisone metabolite urine tetrahydrocortisone. In healthy adults administered a single dose of 10, 20, or 50 mg SPI-62 (n=40), the least squares mean (standard error) tetrahydrocortisone was 32.71 (1.149) mol compared to 9.19 (2.300) mol after a single dose of matching placebo (n=10). In the same subjects after 14 daily doses, tetrahydrocortisone was 42.73 (1.968) mol for SPI-62 and 8.51 (0.410) mol for placebo. Similar results were also observed in elderly adults. Previous studies have also shown that liver cortisone levels increased substantially with ABT-384 administration to healthy adults and elderly subjects for 7-21 days, as evidenced by increases of urine tetrahydrocortisone. Circulating cortisone levels increased substantially, while serum cortisol did not change, in patients with painful diabetic peripheral neuropathy given 10 mg of SPI-62 for 6 weeks. For example, on the last day of study drug administration, serum cortisone was 56.0 (2.37) nM for SPI-62 (n=36) and 38.8 (2.16) nM for placebo (n=36). In addition, two weeks later, serum cortisone was 49.5 (1.75) nM for SPI-62 and 38.7 (1.70) nM for placebo. Similar results on cortisone were not obtained in healthy adults.

Urinary Tetrahydrocortisols

In some embodiments, a pseudo-irreversible HSD-1 inhibitor may be administered to a patient to reduce the levels of urinary tetrahydrocortisols in a patient. The major excretory route of cortisol is as urinary metabolites. The total of these metabolites best represents the total glandular output of cortisol for the day. Cortisol is predominantly excreted as 5-alpha-tetrahydrocortisol (5α-THF) and 5-beta-tetrahydrocortisol (5β-THF), and tetrahydrocortisone (THE). Less abundant urinary metabolites include cortols and cortolone. A small proportion (1-3%) is excreted as cortisol and cortisone, which itself is a metabolite of cortisol. Measurement of urinary cortisol and urinary tetrahydrocortisols over 24 hours can be used to indicate the daily level of cortisol production in the patient. Also provided is a method of reducing the levels of urinary tetrahydrocortisols in a patient, comprising administering to the patient a pseudo-irreversible HSD-1 inhibitor, wherein the levels of said urinary tetrahydrocortisols are elevated compared to an asymptomatic patient.

Pseudo-Irreversible HSD-1 Inhibitor Compound Structures

A number of pseudo-irreversible HSD-1 inhibitors are known and available in the art, including, but not limited to, SPI-62, ABT-384, MK-0736, MK-0916, BMS-823778, UE-2343, AMG-221, KR-67607, BI-187004, SAR-184481, Compound A, Compound B, Compound C, Compound D, BMS-823778, or a pharmaceutically acceptable salt thereof. As would be understood by one of skill in the art, any pseudo-irreversible HSD-1 inhibitor described herein or known or available in the art may be used as described herein and is encompassed within the scope of the present disclosure.

The structures of some pseudo-irreversible HSD-1 inhibitors described herein are set forth below. All structures and IUPAC names were generated using ChemDraw 20.0.

As used herein, "SPI-62" refers to 4-(5-(2-(4-chloro-2,6-difluorophenoxy)propan-2-yl)-4-methyl-4H-1,2,4-triazol-3-yl)-3-fluorobenzamide.

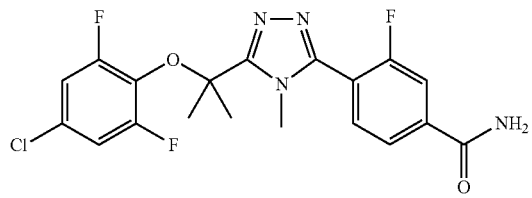 [SMILES: Cn1c(-c2ccc(C(N)=O)cc2F)nnc1C(C)(C)Oc1c(F)cc(Cl)cc1F]

As used herein, "BMS-823778" refers to 2-(3-(1-(4-chlorophenyl)cyclopropyl)-[1,2,4]triazolo[4,3-a]pyridin-8-yl)propan-2-ol.

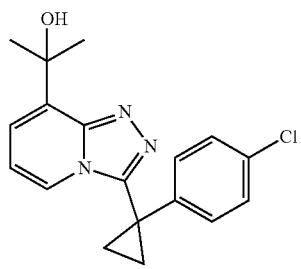 [SMILES: CC(C)(O)c1cccn2c(C3(c4ccc(Cl)cc4)CC3)nnc12]

As used herein, "ABT-384" refers to (1s,3R,4r,5S,7s)-4-(2-methyl-2-(4-(5-(trifluoromethyl)pyridin-2-yl)piperazin-1-yl)propanamido)adamantane-1-carboxamide.

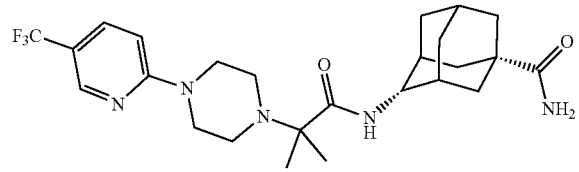 [SMILES: CC(C)(C(=O)N[C@H]1C2CC3CC1C[C@@](C(N)=O)(C3)C2)N1CCN(c2ccc(C(F)(F)F)cn2)CC1]

As used herein, "UE-2343" refers to (5-(1H-pyrazol-4-yl)thiophen-3-yl)((1R,3r,5S)-3-hydroxy-3-(pyrimidin-2-yl)-8-azabicyclo[3.2.1]octan-8-yl)methanone.

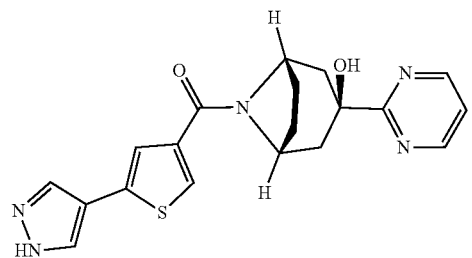

As used herein, "MK-0736" refers to 3-(4-(3-(ethylsulfonyl)propyl)bicyclo[2.2.2]octan-1-yl)-4-methyl-5-(2-(trifluoromethyl)phenyl)-4H-1,2,4-triazole.

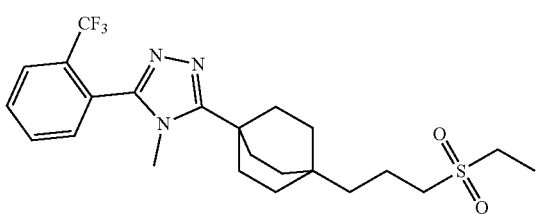 [SMILES: CCS(=O)(=O)CCCC12CCC(c3nnc(-c4ccccc4C(F)(F)F)n3C)(CC1)CC2]

As used herein, "AMG-221" refers to (S,E)-2-(((1S,2S,4R)-bicyclo[2.2.1]heptan-2-yl)imino)-5-isopropyl-5-methylthiazolidin-4-one.

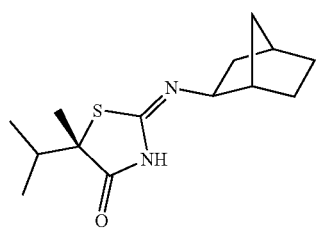 [SMILES: CC(C)[C@]1(C)S/C(=N/C2CC3CCC2C3)NC1=O]

As used herein, "MK-0916" refers to 3-((1s,3s)-1-(4-chlorophenyl)-3-fluorocyclobutyl)-4,5-dicyclopropyl-4H-1,2,4-triazole.

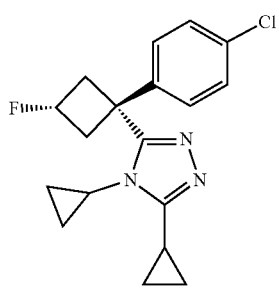 [SMILES: F[C@H]1C[C@@](c2ccc(Cl)cc2)(c2nnc(C3CC3)n2C2CC2)C1]

As used herein, "KR-67607" refers to (1s,3R,4s,5S,7s)-4-(2-(6-(2,6-dichloro-4-(trifluoromethyl)phenyl)-4-methyl-1,1-dioxido-1,2,6-thiadiazinan-2-yl)acetamido)adamantane-1-carboxamide.

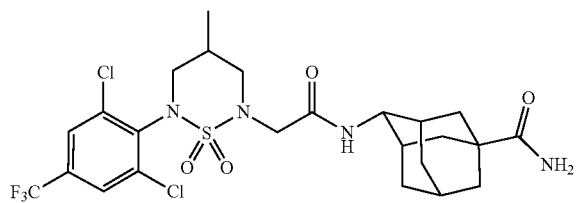 [SMILES: CC1CN(CC(=O)NC2C3CC4CC2CC(C(N)=O)(C4)C3)S(=O)(=O)N(c2c(Cl)cc(C(F)(F)F)cc2Cl)C1]

As used herein, "BI-187004" refers to (4aR,9aS)-1-(1H-benzo[d]imidazole-6-carbonyl)-2,3,4,4a,9,9a-hexahydro-1H-indeno[2,1-b]pyridine-6-carbonitrile.

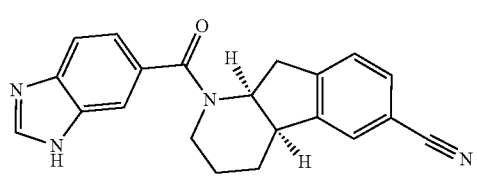 [SMILES: N#Cc1ccc2c(c1)[C@H]1CCCN(C(=O)c3ccc4nc[nH]c4c3)[C@H]1C2]

As used herein, "AZD4017" refers to (S)-2-(1-(5-(cyclohexylcarbamoyl)-6-(propylthio)pyridin-2-yl)piperidin-3-yl)acetic acid.

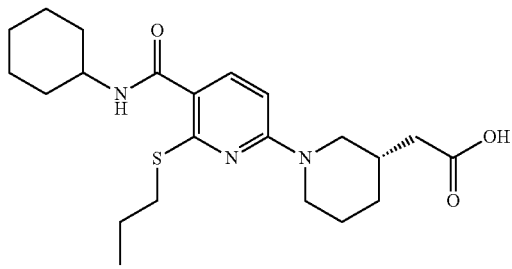 [SMILES: CCCSc1nc(N2CCC[C@@H](CC(=O)O)C2)ccc1C(=O)NC1CCCCC1]

As used herein, "AZD8329" refers to 4-(4-(((1r,3r,5r,7r)-adamantan-2-yl)carbamoyl)-5-(tert-butyl)-1H-pyrazol-1-yl)benzoic acid.

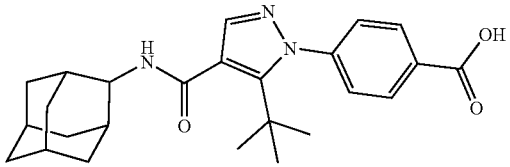

As used herein, "BI-135585" refers to (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one.

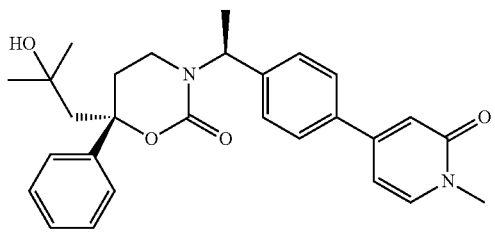 [SMILES: C[C@@H](c1ccc(-c2ccn(C)c(=O)c2)cc1)N1CC[C@](CC(C)(C)O)(c2ccccc2)OC1=O]

As used herein, "SAR-184841" refers to 4-(5-(4-(tert-butyl)piperazin-1-yl)pyridin-2-yl)-N-((1R,3S,5s,7s)-5-carbamoyladamantan-2-yl)-3,4-dihydroquinoxaline-1(2H)-carboxamide.

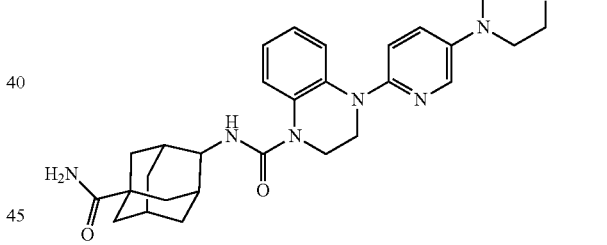

As used herein, "Compound A" refers to (1s,3R,5S,7s)-4-(2-(4-methoxyphenoxy)-2-methylpropanamido)adamantane-1-carboxamide.

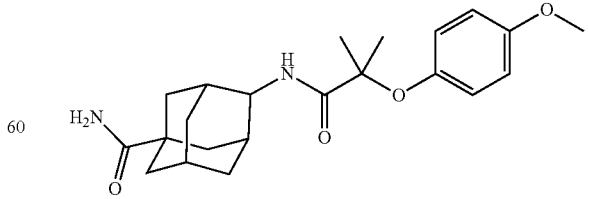

As used herein, "Compound B" refers to 3,4-dihydroquinolin-1(2H)-yl[4-(1H-imidazol-5-yl)piperidin-1-yl]methanone.

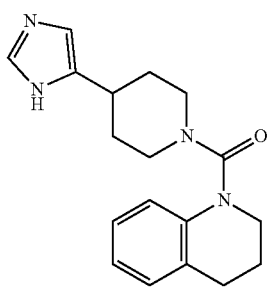 [SMILES: O=C(N1CCC(c2cnc[nH]2)CC1)N1CCCc2ccccc21]

As used herein, "Compound C" refers to (5R)-2-[(2-fluorophenyl)amino]-5-(1-methylethyl)-1,3-thiazol-4(5H)-one.

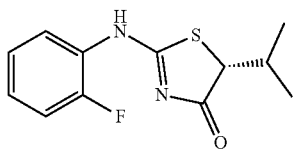 [SMILES: CC(C)[C@H]1SC(Nc2ccccc2F)=NC1=O]

As used herein, "Compound D" refers to 3-(2-fluoroethyl)-4-((4-[(2S)-1,1,1-trifluoro-2-hydroxypropan-2-yl]phenyl)sulfonyl)benzonitrile.

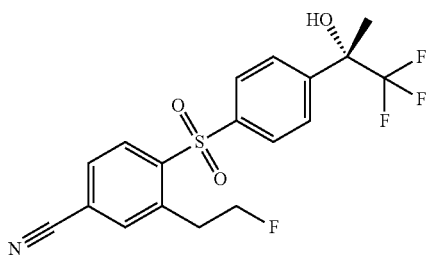 [SMILES: C[C@](O)(c1ccc(S(=O)(=O)c2ccc(C#N)cc2CCF)cc1)C(F)(F)F]

Symptoms of Glucocorticoid Excess

Also provided is a method to treat or improve specific symptoms of a patient with GC excess by administration of a pseudo-irreversible HSD-1 inhibitor. Symptoms of GC excess can vary depending on the individual, though common symptom domains can include, but are not limited to, cardiovascular, metabolic, immunologic, osteal, muscular, dermatological, ocular, psychiatric, cognitive, circadian, and homeostatic. In some embodiments, brain-penetrant pseudo-irreversible HSD-1 inhibitors can be used to treat symptoms relating to mood, cognition, and sleep.

In some embodiments, specific symptoms relating to GC excess can include, but are not limited to, weight gain and fatty tissue deposits, particularly around the midsection and upper back, in the face, and between the shoulders, pink or purple stretch marks (striae) on the skin of the abdomen, thighs, breasts and arms, thinning, fragile skin that bruises easily, fatigue, getting sick often, bruising and slow wound healing, weak bones, muscle weakness, high blood sugar, anxiety and depression, sleep problems, and difficulty concentrating. In some embodiments, long-term high cortisol can result in heart disease, osteoporosis, diabetes, and poor mental health.

In some embodiments, cardiovascular symptoms associated with GC excess can include, but are not limited to, hypertension (including lack of nocturnal blood pressure dipping), atherosclerosis, endothelial dysfunction, prothrombic state, coronary artery disease, heart failure, and stroke.

In some embodiments, metabolic symptoms associated with GC excess can include, but are not limited to, obesity, glucose intolerance, insulin resistance, diabetes, and dyslipidemia (including hypercholesterolemia and hypertriglyceridemia).

In some embodiments, immunologic symptoms associated with GC excess can include, but are not limited to, infections (including opportunistic infections) and sepsis.

In some embodiments, osteal symptoms associated with GC excess can include, but are not limited to, osteoporosis, osteonecrosis, osteopenia, hypocalcemia (via decreased absorption or increased renal elimination or effects on vitamin D and PTH), impaired linear bone growth (stature), and fractures (including low-impact or compression fractures).

In some embodiments, muscular symptoms associated with GC excess can include, but are not limited to, muscle atrophy and muscle weakness.

In some embodiments, dermatological symptoms associated with GC excess can include, but are not limited to, impaired wound healing, thin or fragile skin, abnormal accumulations of subcutaneous fat, plethora, violaceous striae, acanthosis nigricans, hyperpigmentation, and easy bruisability.

In some embodiments, ocular symptoms associated with GC excess can include, but are not limited to, increased ocular pressure, glaucoma, exophthalmos, and cataract.

In some embodiments, psychiatric symptoms associated with GC excess can include, but are not limited to, depression, anxiety, hypomania, mania, and psychosis.

In some embodiments, cognitive symptoms associated with GC excess can include, but are not limited to, impairments in memory, visuospatial processing, reasoning, verbal learning, and language performance.

In some embodiments, circadian symptoms associated with GC excess can include, but are not limited to, insomnia, daytime fatigue, sleep apnea, fragmented sleep, increased nocturnal motor activity, and abnormal REM sleep.

In some embodiments, homeostatic symptoms associated with GC excess can include, but are not limited to, hypokalemia, hypernatremia, hypophosphatemia, hypercalciuria, suppressed growth hormone, and thyroid disease (including hypothyroidism and hyperthyroidism).

Lack of Adipose Tachyphylaxis

Also provided is a method to treat or improve glucocorticoid excess or symptoms thereof in a patient by administration of a pseudo-irreversible HSD-1 inhibitor that does not show tachyphylaxis for human adipose HSD-1 inhibition. Competition by increased HSD-1 substrate (inactive GC) levels can lead to adipose tachyphylaxis. GC are highly lipophilic, whether in an active or inactive form, and thus accumulation of GC in tissues of a patient given an HSD-1 inhibitor would be expected, particularly a patient with GC excess and also particularly in adipose tissue, as described herein.

In some embodiments, a pseudo-irreversible HSD-1 inhibitor useful for the present disclosure may be any pseudo-irreversible HSD-1 inhibitor known or available in the art. Some exemplary pseudo-irreversible HSD-1 inhibitors include, but are not limited to, SPI-62, ABT-384, MK-0736, MK-0916, BMS-823778, UE-2343, AMG-221, KR-67607, BI-187004, SAR-184481, Compound A, Compound B, Compound C, Compound D, or a pharmaceutically acceptable salt thereof. One of skill in the art will recognize that other pseudo-irreversible HSD-1 inhibitors may be used without deviating from the scope of the present disclosure. In some embodiments, the pseudo-irreversible HSD-1 inhibitor is selected from SPI-62, ABT-384, KR-67607, SAR-184481, Compound A, and Compound B, or a pharmaceutically acceptable salt thereof. In some embodiments, the pseudo-irreversible HSD-1 inhibitor is selected from BMS-823778, MK-0916, Compound C, and Compound D, or a pharmaceutically acceptable salt thereof. In some embodiments, the pseudo-irreversible HSD-1 inhibitor is selected from SPI-62, ABT-384, MK-0736, MK-0916, BMS-823778, UE-2343, and AMG-221, or a pharmaceutically acceptable salt thereof. In some embodiments, the pseudo-irreversible HSD-1 inhibitor is selected from SPI-62, ABT-384, KR-67607, UE-2343, and BI-187004, or a pharmaceutically acceptable salt thereof. In some embodiments, the pseudo-irreversible HSD-1 inhibitor is selected from SPI-62 and ABT-384, or a pharmaceutically acceptable salt thereof. In some embodiments, the pseudo-irreversible HSD-1 inhibitor is SPI-62, or a pharmaceutically acceptable salt thereof.

In some embodiments, a pseudo-irreversible HSD-1 inhibitor as described herein is administered to a patient or subject having elevated levels of glucocorticoids or urinary tetrahydrocortisols in order to reduce the levels of the glucocorticoids or urinary tetrahydrocortisols in the patient or subject. In some embodiments, administration of the pseudo-irreversible HSD-1 inhibitor may be paused or discontinued once symptoms are reduced or eliminated in the patient and may be restarted as necessary if deemed appropriate by a clinician or physician. In some embodiments, the disclosure provides chronic treatment of a patient with administration of a pseudo-irreversible HSD-1 inhibitor, without pause or discontinuation, for chronic GC excess conditions. In some embodiments, pseudo-irreversible inhibitors provide an advantage in that they retain efficacy during short drug cessation (e.g., a patient neglecting to take their medication for a few days or even weeks).

In some embodiments, the dosage of a pseudo-irreversible HSD-1 inhibitor as described herein may be any dosage deemed appropriate by a practitioner or clinician. In some embodiments, a pseudo-irreversible inhibitor is administered at a molar dose sufficient to occupy all HSD-1 in the body. In some embodiments, a pseudo-irreversible HSD-1 inhibitor achieves and maintains full target engagement at low doses. In some embodiments, pseudo-irreversible HSD-1 inhibitors achieve and maintain full target engagement at sub-milligram doses.

In some embodiments, a pseudo-irreversible HSD-1 inhibitor is administered in a single dose of from about 1 to about 40 mg, including 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, or the like. In some embodiments, a sub-milligram dose may be any dose about equal to, or less than, 1 mg, such as 0.05 mg, 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, or 1 mg. In some embodiments, a single dose of a pseudo-irreversible HSD-1 inhibitor may be appropriate for a patient with chronic GC excess as described herein. In some embodiments, a single dose of a pseudo-irreversible inhibitor is administered intravenously.

In some embodiments, a pseudo-irreversible HSD-1 inhibitor may be administered in multiple doses for a specified period of time. Multiple doses may refer to multiple doses in a single day, or, alternatively, may refer to single doses per day for a period of time deemed appropriate by a clinician or practitioner.

In some embodiments, a dose range for SPI-62 is from about 0.2 to about 6 mg once daily. In some embodiments, a dose of SPI-62, ABT-384, MK-0736 or MK-0916 is about 10 mg or less. In some embodiments, a dose of UE-2343 is from about 10 mg to about 35 mg. In some embodiments, a dose of BI-187004 is from about 20 mg to about 240 mg.

In some embodiments, a period of time for administration of a pseudo-irreversible HSD-1 inhibitor may be any period of time, such as including, but not limited to, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or the like. A period of time in accordance with the present disclosure may be, any period of time, for example, a period of 1-14 days, or 7-14 days, or 7-10 days, or 10-14 days. In other embodiments, a period of time for administration of an HSD-1 inhibitor may be from 7-30 days, or 7-21 days, or the like. In some embodiments, a period of time for administration of a pseudo-irreversible HSD-1 inhibitor may be 1 day, 6 days, or 12 days. In some embodiments, a pseudo-irreversible HSD-1 inhibitor may be administered to a patient on a continual basis to control chronic GC excess. In some embodiments, administration of a dosage of a pseudo-irreversible HSD-1 inhibitor may be for 1 month, or 2 months, or 3 months, or 4 months, or 5 months, or 6 months, or 7 months, or 8 months, or 9 months, or 10 months, or 11 months, or 12 months, or 15 months, or 18 months, or 24 months, or 36 months, or 48 months, or longer. In some embodiments, a pseudo-irreversible HSD-1 inhibitor may be administered intravenously in a single high dose, for example to control sepsis or to prevent the development of side effects of steroid use, e.g., in diabetic patients.

As described herein, a pseudo-irreversible HSD-1 inhibitor (1) should not show adipose tachyphylaxis, (2) should show TMDD PK & PD, (3) should show fast-on slow-off kinetics, and (4) should link to NADPH in the active site. However, only one of these characteristics is necessary to indicate that a molecule is a pseudo-irreversible HSD-1 inhibitor.

In some embodiments, a pseudo-irreversible HSD-1 inhibitor as described herein (e.g., SPI-62, ABT-384, etc.) is characterized by human pharmacokinetics consistent with target-mediated drug disposition as described herein.

In some embodiments, the pseudo-irreversible HSD-1 inhibitor has a long pharmacodynamic half-life for human hepatic HSD-1 inhibition. In some embodiments, the pharmacodynamic half-life of the HSD-1 inhibitor for hepatic HSD-1 inhibition is extended compared to its pharmacokinetic half-life. In some embodiments, the half-life for human hepatic HSD-1 inhibition is at least 1 week, or 2 weeks, or 3 weeks, or 4 weeks, or 5 weeks, or 6 weeks, or the like.

In some embodiments, the pseudo-irreversible HSD-1 inhibitor shows fast-on, slow-off binding kinetics to human HSD-1. In some embodiments, residence time is an indicator of fast-on slow-off binding kinetics for an HSD-1 inhibitor. Pseudo-irreversible HSD-1 inhibitors can be identified via in vitro enzyme kinetics evaluation, in which they are expected to show longer enzyme residence times compared to other HSD-1 inhibitors. In some embodiments, an HSD-1 inhibitor as described herein shows residence time of at least about 500 seconds. As would be understood by one of skill in the art, residence time threshold may vary with different buffers, NADPH concentrations, or enzyme concentrations.

In some embodiments, an initial dose of a pseudo-irreversible HSD-1 inhibitor initially binds to, and remains bound to, its target in tissues. In some embodiments, up to about 3 mg of the pseudo-irreversible HSD-1 inhibitor is sequestered from central circulation. In some embodiments, the pseudo-irreversible HSD-1 inhibitor exhibits nonlinear pharmacokinetics after a single dose in the sub-milligram to low-milligram range, with dose-proportional exposures after multiple doses. In some embodiments, plasma exposures of the HSD-1 inhibitor are less than dose-proportional after low single doses and dose-proportional after multiple low doses. In some embodiments, the doses are 10 mg or lower, e.g., 10 mg, or 9 mg, or 8 mg, or 7 mg, or 6 mg, or 5 mg, or 4 mg, or 3 mg, or 2 mg, or 1 mg, or less than 1 mg. In some embodiments, the doses are 6 mg or lower, or 4 mg or lower.

In some embodiments, the pharmacokinetics of the pseudo-irreversible HSD-1 inhibitor, e.g., SPI-62, is characterized by a two-compartment TMDD population pharmacokinetics model with 3 transit absorption compartments and an estimated target capacity of about 2.5 to 3.6 mg. In some embodiments, the pseudo-irreversible HSD-1 inhibitor has a $K_d$ lower than the $K_i$. In some embodiments, the pseudo-irreversible HSD-1 inhibitor has a $K_d$ at least 10-fold lower than the $K_i$. In some embodiments, the pseudo-irreversible HSD-1 inhibitor has a $K_d$ at least 60-fold lower than the $K_i$. In some embodiments, the pseudo-irreversible HSD-1 inhibitor has an in vivo $IC_{50}$ for hepatic HSD-1 at least 50-fold lower than measured in vitro. In some embodiments, the pseudo-irreversible HSD-1 inhibitor has an in vivo $IC_{50}$ for hepatic HSD-1 approximately 200-fold lower than measured in vitro. In some embodiments, the pseudo-irreversible HSD-1 inhibitor has an estimated in vivo adipose $IC_{50}$ for HSD-1 lower than that of the HSD-1 inhibitor measured in vitro. In some embodiments, the pseudo-irreversible HSD-1 inhibitor has an in vivo adipose $IC_{50}$ at least 100-fold lower than measured in vitro. In some embodiments, the pseudo-irreversible HSD-1 inhibitor has an in vivo adipose $IC_{50}$ approximately 700-fold lower than measured in vitro.

In some embodiments, a pseudo-irreversible HSD-1 inhibitor may be co-administered along with a glucocorticoid medication. In some embodiments, the pseudo-irreversible HSD-1 inhibitor and the glucocorticoid medication are co-administered in a fixed-dose combination, co-packaged, or prescribed separately. As described herein, a glucocorticoid medication may be glucocorticoid known or available in the art, such as including, but not limited to, prednisolone, methylprednisolone, dexamethasone, hydrocortisone, budesonide, deflazacort, beclomethasone, ciclesonide, fluticasone, mometasone, triamcinolone, flunisolide, clobetasol, betamethasone, fluocinonide, flurandrenolide, clocortolone, halobetasol, desoximetasone, desonide, halcinonide, prednicarbate, diflorasone, amcinonide, alclometasone, difluprednate, loteprednol, fluoromethalone, rimexolone, and medrysone. Ester prodrugs of glucocorticoids (e.g., prednisolone acetate and prednisolone hemisuccinate), or a pharmaceutically acceptable salt thereof, which are administered to extend the duration of pharmacological effect, are also suitable and encompassed within the scope of the present disclosure. In some embodiments, the specific glucocorticoid medication may vary as deemed appropriate by a practitioner or clinician. In some embodiments, the glucocorticoid medication may not be prednisone or cortisone, which are inactive prodrugs that require HSD-1 for activation.

In some embodiments, a pseudo-irreversible HSD-1 inhibitor as described herein may be administered by any route deemed appropriate by a practitioner or clinician. Suitable routes of administration include, but are not limited to, oral, intravenous, intramuscular, subcutaneous, inhalation, intranasal, ocular, topical.

Definitions

The definitions and methods provided define the present disclosure and guide those of ordinary skill in the art in the practice of the present disclosure. Unless otherwise noted, terms are to be understood according to conventional usage by those of ordinary skill in the relevant art.

As used herein, "brain penetrant" refers to a drug or compound that crosses the blood-brain barrier. In some embodiments, a brain penetrant pseudo-irreversible HSD-1 inhibitor is used to treat symptoms of glucocorticoid excess relating to mood, cognitive abilities, and sleep.

As used herein, "glucocorticoid excess" refers to a condition or physiological state in an individual in which the levels of active glucocorticoids e.g., cortisol or a synthetic glucocorticoid, is elevated relative to a reference patient or sample, or relative to a patient not experiencing glucocorticoid excess.

As used herein, a "pseudo-irreversible HSD-1 inhibitor" refers to a compound, such as a small molecule compound that bind to, interacts with, elicits a conformational change, or otherwise inhibits or abolishes the activity of HSD-1.

As used herein, "pseudo-irreversible inhibition" refers to hydrogen bonding or aromatic stacking interactions with the NADPH cofactor of HSD-1 and the inhibitor molecule. Through these, a ternary complex is formed that is more resistant to dissociation (i.e., stronger binding, not weaker) compared to other HSD-1 inhibitors that form only binary complexes with the enzyme.

As used herein, "tachyphylaxis" refers to diminishing response to successive doses of a drug, rendering the drug less effective. Tachyphylaxis refers to an onset of drug insensitivity.

As used herein, an "effective amount" of a compound refers to an amount that is sufficient to generate a desired response, such as reduce or eliminate a sign or symptom of a condition or disease. For instance, as described herein, an effective amount may be an amount of a pseudo-irreversible HSD-1 inhibitor necessary to treat glucocorticoid excess in a patient. An effective amount of a pseudo-irreversible HSD-1 inhibitor may be an amount necessary to improve or prevent symptoms of glucocorticoid excess in a patient, or to reduce the levels of urinary tetrahydrocortisols in a patient. In general, this amount will be sufficient to measurably reduce symptoms of glucocorticoid excess or reduce the levels of urinary tetrahydrocortisols in a patient. When administered to a subject, a dosage will generally be used that will achieve target tissue concentrations (e.g., in liver, adipose tissue, brain, bone, muscle, skin, eye) that has been shown to achieve an acceptable level of glucocorticoids or urinary tetrahydrocortisols, i.e., a level that does not cause symptoms of glucocorticoid excess in the patient. In some examples, an "effective amount" is one that treats one or more symptoms. In one example, an effective amount is a therapeutically effective amount. In one example, an effective amount is an amount that prevents or reverses one or more signs or symptoms of glucocorticoid excess.

As used herein, "reducing" or "reduced" refers to a lowering or reduction in amount or levels of, e.g., one or more glucocorticoids or urinary tetrahydrocortisols in a patient relative to a reference sample or patient. As used herein, reducing the amount refers to reducing the level of glucocorticoids or urinary tetrahydrocortisols to a level in which physiological symptoms are not found or do not occur in the patient.

As used herein, a "reference sample" or "reference patient" is a sample or patient to whom a pseudo-irreversible HSD-1 inhibitor was not administered as described herein, or a healthy patient.

As used herein, "subject" or "patient" refers to a human. A patient or subject in accordance with the present disclosure has glucocorticoid excess. Unless otherwise noted, the terms "patient" or "subject" are used herein interchangeably. In some embodiments, a patient or subject as described herein has an ACTH- or CRH-secreting tumor. In some embodiments, the patient or subject has a cortisol-secreting tumor.

As used herein, "tetrohydrocortisols" refers to urinary tetrahydrocortisol or cortols, the levels of which are altered by administration of an HSD-1 inhibitor.

The term "treating" or "alleviating" includes the administration of compounds or agents to a patient for alleviating or reversing the symptoms, or arresting or inhibiting further development, of a disease, condition, or disorder. Subjects in need of treatment include those already suffering from the disease or disorder or experiencing symptoms of a disease, condition, or disorder, e.g., patients having elevated levels of glucocorticoids or urinary tetrahydrocortisols.

Numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes a measure of variability for the device or method being employed to determine the value. The numerical parameters set forth in the written description and attached claims are approximations that can vary depending upon the desired properties sought to be obtained by a particular embodiment. The numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the variability found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

The terms "a," and "an," and "the," and similar references used in the context of describing a particular embodiment (especially in the context of certain of the following claims) can be construed to cover both the singular and the plural, unless specifically noted otherwise. The term "or" as used herein, including the claims, is used inclusively unless explicitly indicated to refer to alternatives only or the alternatives are mutually exclusive.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and can also cover other unlisted steps. Similarly, any composition or device that "comprises," "has," or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

Examples of embodiments of the present disclosure are provided in the following examples. The following examples are presented only by way of illustration and to assist one of ordinary skill in using the disclosure. The examples are not intended in any way to otherwise limit the scope of the disclosure.

Example 1. Adipose HSD-1 Inhibition by SPI-62

A paradoxical observation reported for 3 HSD-1 inhibitors, and potentially considered to be a class effect, is tachyphylaxis of human adipose HSD-1 inhibition. The following HSD-1 inhibitors showed more adipose HSD-1 inhibition after a single dose compared to after multiple doses, even as plasma drug levels increased to steady state with repeated dosing and liver HSD-1 inhibition was observed after both single and multiple doses.

In abdominally obese subjects, AZD4017 demonstrated adipose HSD-1 inhibition after a single dose, yet no sustained inhibitory effect after repeated dosing. AZD4017 also showed no skin HSD-1 inhibition after multiple doses, although in the same subjects it was associated with maximal liver HSD-1 inhibition. As there are no data after a single dose, it is unknown whether AZD4017 showed tachyphylaxis of skin HSD-1 inhibition or whether there may be another explanation. Clinical benefit in skin (improved wound healing) was observed in subjects who received AZD4017 compared to those who received placebo. It is possible that the ex vivo assay used to measure skin HSD-1 activity was not specific.

In human adipose tissue, inhibition of HSD-1 activity was lost after repeat dosing of AZD8329, compared with acute administration.

Median HSD-1 enzyme inhibition in human adipose tissue reached 90% after a single dose of BI-135585 but was low (31% or lower) after 14 days of continuous treatment.

It was predicted that pseudo-irreversible HSD-1 inhibitors would not show tachyphylaxis of human adipose HSD-1 inhibition. This was based on a hypothesis that adipose tachyphylaxis is a consequence of competition by increased HSD-1 substrate (inactive GC) levels. Inactive GCs are highly lipophilic and therefore would be expected to accumulate in tissues of a patient treated with an HSD-1 inhibitor, particularly a patient with GC excess and also particularly in adipose tissue.

BI-187004, identified by us as a pseudo-irreversible HSD-1 inhibitor based on fast-on slow-off in vitro enzyme kinetics, showed limited tachyphylaxis of human adipose HSD-1 inhibition. For example, median HSD-1 enzyme inhibition in human adipose tissue associated with a 20 mg dose was 92.4% on Day 2 and 78.1% on Day 15. For a 240 mg dose, the medians were 99.5% on Day 2 and 93.1% on Day 15. Differences between Day 2 and Day 15 may be because adipose samples were, for logistical reasons, obtained 10 to 45 minutes after a dose on Day 2 and 24 hours after the Day 14 dose on Day 15.

Cortisone is an endogenous HSD-1 substrate with $K_m$ of 1.9 mM and log P of 1.25. Prednisone is a common GC medication, a prodrug that requires HSD-1 for activation to prednisolone. It is also a major metabolite of prednisolone, another common GC medication. It has $K_m$ of 20.6 mM for human HSD-1 and log P of 1.5.

Increased tissue levels of cortisone, prednisone, or other lipophilic HSD-1 substrates are problematic for a competitive inhibitor such as AZD4017, AZD8329, or BI-135585. As substrate, such as cortisone or prednisone, accumulates in a tissue because HSD-1 does not convert it to an active form it can compete off the inhibitor. This is consistent with the observation that those 3 compounds inhibit adipose HSD-1 substantially after a single dose but less so after multiple doses. This phenomenon may be more prevalent in adipose (and perhaps skin) compared to liver because of lower tissue blood flow, higher lipid content, and perhaps other factors. In contrast, a pseudo-irreversible inhibitor would be much less susceptible to competition by substrate accumulation and much more able to maintain HSD-1 inhibition and the attendant clinical benefits thereof. The prediction was verified in a clinical trial.

Male and non-menstruating female subjects with type 2 diabetes aged between 18 and 65 years with a body mass index between 30.0 and 45.0 were administered SPI-62 daily for 14 days. For at least 4 hours prior to, and throughout, the $1^{st}$, $2^{nd}$ and $14^{th}$ dose intervals, D8 cortisone ([2,2,4,6,6,9,12,12-$^2$H$_8$] cortisone, Millipore Sigma, Miamisburg OH) 1 μg/mL in Perfusion Fluid T1 (M Dialysis, Stockholm Sweden)+0.5% alcohol USP was infused continuously into subcutaneous abdominal adipose tissue via microdialysis catheters (63 Microdialysis Catheter, MDialysis, Stockholm Sweden) at a rate of 1 μL/min. Adipose dialysate was collected for two-hour intervals (0-2, 2-4, 4-6, 6-8, 8-10, 20-22, and 22-24 hours after the SPI-62 dose) and analyzed for D8 cortisone and D8 cortisol. D8 cortisol mole percent fraction (MPF) was calculated as: ([2,2,4,6,6,9,12,12-$^2$H$_8$] cortisol*368.51)/([2,2,4,6,6,9,12,12-$^2$H$_8$] cortisone*370.52), where 368.51 and 370.52 are the molar masses of D8 cortisone and D8 cortisol. Percent adipose HSD-1 inhibition was calculated as: $100*(1-(MPF_t/MPF_{baseline}))$.

The time (t) of the sample was considered to be the midpoint of the collection interval. Assay sensitivity limited quantitation of adipose HSD-1 inhibition to ~90-95%, depending on the value of D8 cortisone, as D8 cortisol values below the lower limit of quantitation were imputed as the lower limit of quantitation. Data shown are the median inhibition observed in two subjects for whom the SPI-62 daily dose was 6 mg.

As shown in FIG. 1, adipose HSD-1 inhibition was detected between 2-4 hours after a single dose, reached maximal measurable levels during the $2^{nd}$ dose interval, and was almost identical during the $2^{nd}$ and $14^{th}$ dose intervals. In additional subjects for whom the SPI-62 dose was 1, 2, 3, or 10 mg, maximum measurable adipose HSD-1 inhibition was observed after multiple doses even though no or limited adipose HSD-1 inhibition was associated with the lower single SPI-62 doses.

Example 2. Pseudo-Irreversible HSD-1 Inhibitors Identified by Human Pharmacokinetics Pseudo-irreversible HSD-1 inhibitors can be identified via human pharmacokinetic data. As an initial dose of a pseudo-irreversible HSD-1 inhibitor initially binds to, and remains bound to, its target in tissues, up to ~3 mg can be sequestered from central circulation. Accordingly, there is striking and consistent nonlinearity of pharmacokinetics after single doses in the sub-mg to low-mg range, with dose-proportional exposures after multiple doses. The following are identified as pseudo-irreversible HSD-1 inhibitors based on human pharmacokinetic data.

Following administration of single SPI-62 (formerly ASP3662) doses, substantial non-linearity of plasma exposures was observed; single doses of 0.7 to 3 mg were associated with dose-normalized plasma levels much lower than were higher single doses. Plasma levels after 14 days of dosing were approximately dose-proportional for SPI-62 doses of 0.2 to 50 mg (a 3 mg loading dose was administered prior to daily 0.2 mg dosing). The single- and multiple-dose pharmacokinetics of SPI-62 were well-characterized by a two-compartment TMDD population pharmacokinetics model with 3 transit absorption compartments and an estimated target capacity of ~2.5 mg of SPI-62 which comports well with the dose range in which pharmacokinetic nonlinearity is prominent.

Following administration of single ABT-384 doses, substantial non-linearity of plasma exposures was observed; single doses of 1 to 4 mg were associated with dose-normalized plasma levels much lower than were higher single doses. Plasma levels after 14 days of dosing were approximately dose-proportional for ABT-384 doses of 1 to 100 mg. The single- and multiple-dose pharmacokinetics of ABT-384 were well-characterized by a two-compartment TMDD population pharmacokinetics model with 3 transit absorption compartments and an estimated target capacity of ~1 mg of SPI-62, which comports well with the dose range in which pharmacokinetic nonlinearity is prominent and is potentially a low estimate because no data from sub-mg doses were available. ABT-384 was reported to be retained for at least 77 days in cynomolgus monkey liver.

SPI-62 and ABT-384 share the remarkable and unexpected property of a $K_d$ approximately 60-fold lower than the $K_i$.

MK-0736 exhibited non-linear, saturable distribution PK that resulted in decreased half-life with increased dose and dose dependent accumulation. Population pharmacokinetics of MK-0736 was described by a two-compartment model with first-order absorption, linear elimination, and saturable distribution. The range of administered doses was 1.2 to 200 mg, such that the saturable distribution was likely observed at doses similar to SPI-62 and ABT-384 which is consistent with those precedents for HSD-1 inhibitor TMDD. The authors, clinical pharmacology experts from Merck, were apparently unaware of TMDD so used a less suitable model structure to model MK-0736 pharmacokinetics.

Following administration of single MK-0916 doses, substantial non-linearity of plasma exposures was observed; single doses of 0.2 to 3.16 mg were associated with dose-normalized plasma levels much lower than were higher single doses. Plasma levels after 14 or 28 days of dosing were approximately dose-proportional for MK-0916 doses of 0.2 to 50 mg. The pharmacokinetic data were fitted to a two-compartment saturable-distribution model. The range of doses at which pharmacokinetic linearity was observed was similar to SPI-62, suggesting that MK-0916 is also subject to TMDD mediated by HSD-1. The authors, clinical pharmacology experts from Merck, were apparently unaware of TMDD so used a less suitable model structure to model MK-0916 pharmacokinetics. The estimated capacity of saturable distribution of ~3 mg of MK-0916 comports well with the dose range in which pharmacokinetic nonlinearity is prominent as well as the target capacity estimated for SPI-62 using a TMDD model.

BMS-823778 plasma levels were not detected after a single 0.1 or 0.5 mg dose, and less than dose proportional plasma levels after a single 2 mg dose. Steady-state exposures were dose proportional from 0.5 mg daily. Those observations are consistent with HSD-1 inhibitor TMDD clinical pharmacokinetic behavior that is best characterized by SPI-62 and ABT-384. A physiology-based pharmacokinetics model over-predicted exposures after the first dose at low levels. The authors, clinical pharmacology experts from BMS, attributed that weakness of their model to an unknown mechanism so were clearly unaware of TMDD mediated by HSD-1.

UE2343 plasma levels were below the level of quantification after single doses of 2 and 5 mg. Exposures increased in a greater than dose-proportional manner after single doses of 10 to 35 mg. A figure shows that the measured mean maximum plasma concentration after a single 10 mg dose (40.4 ng/mL) was substantially higher than the assay limit of quantitation (by visual inference, no more than ~5 ng/mL). Multiple dose data for doses <10 mg were not reported. A population pharmacokinetic model has not been reported. TMDD due to pseudo-irreversible HSD-1 inhibition by UE2343 is the most likely explanation for the data.

AMG-221 showed nonlinearity of pharmacokinetics, with dose-normalized exposures lower after a single 3 mg dose compared to after single 30 or 100 mg doses. The plasma level data were characterized by a 2-compartment open model with linear elimination from the central compartment which somewhat over-estimated exposures associated with the higher doses. AMG-221 appears to show human pharmacokinetics consistent with TMDD, although without data after repeated dosing, inference is less clear than for other HSD-1 inhibitors based on pharmacokinetic evidence alone.

BI-187004 dose-normalized plasma levels following a single 2.5 mg dose were substantially below, and after a single 5 mg dose were below, those associated with single doses of 10 mg and higher. Multiple dose data below 10 mg were not reported. A population pharmacokinetic model has not been reported. TMDD due to pseudo-irreversible HSD-1 inhibition by BI-187004 is the most likely explanation for the data.

Example 3. Pseudo-Irreversible HSD-1 Inhibitors Identified by Human Pharmacodynamics Pseudo-irreversible HSD-1 inhibitors can be identified via human pharmacodynamic data. Because the inhibitor dissociates slowly from the enzyme, the following are characteristic of pseudo-irreversible HSD-1 inhibitors.

HSD-1 inhibition will be observed for an extended time after dosing cessation, particularly in liver where HSD-1 protein concentration is highest which could further facilitate long-duration interaction. With high HSD-1 concentration in the endoplasmic reticulum, in theory an inhibitor molecule that dissociates from one enzyme molecule has a higher probability to bind to another before distributing out of the endoplasmic reticulum.

Target inhibition can be associated with very low plasma levels. While circulating pseudo-irreversible HSD-1 inhibitor molecules are not bound to enzyme and so may be eliminated by similar routes and with similar rates as other HSD-1 inhibitors, long-duration binding to intracellular enzyme provides a compartment from which a pseudo-irreversible HSD-1 inhibitor re-enters circulation only very slowly. Even with high sensitivity assays, HSD-1 inhibition may be associated with plasma drug levels near or below the limit of quantitation and unbound (i.e., tissue-accessible) levels well below the molecule's $K_i$ or $IC_{50}$ for human HSD-1.

After a single dose, hysteresis and concentration independence will be observed for HSD-1 inhibition. As a pseudo-irreversible HSD-1 inhibitor is absorbed from the gastrointestinal tract, it first distributes to the liver which contains the highest concentration of HSD-1 to which the drug can bind and remain bound without entering central circulation. For low doses, substantial HSD-1 inhibition may be observed before drug achieves plasma levels above the limit of quantitation. Liver HSD-1 inhibition might not change much as drug plasma levels increase and then decrease after a single dose of a pseudo-irreversible HSD-1 inhibitor, particularly if the dose is sufficient to saturate liver HSD-1 (which has a capacity of up to ~3 mg drug in healthy adults).

In hepatocytes, 5- and 3-steroid reductase enzymes sequentially metabolize cortisol (HSD-1 product) to tetrahydrocortisol and allotetrahydrocortisol, and cortisone (HSD-1 substrate) to tetrahydrocortisone. The tetrahydro metabolites are rapidly and extensively excreted in urine. Hence, the urinary ratio (tetrahydrocortisol+allotetrahydrocortisol)/tetrahydrocortisone is a biomarker of liver enzyme activity. Continued adrenal synthesis provides a circulating pool of cortisol, the free fraction of which (~5%) enters cells. That prevents the urinary HSD-1 ratio from dropping below approximately 0.1. Hence values in that range are considered to indicate maximal inhibition of liver HSD-1.

Figure 2:
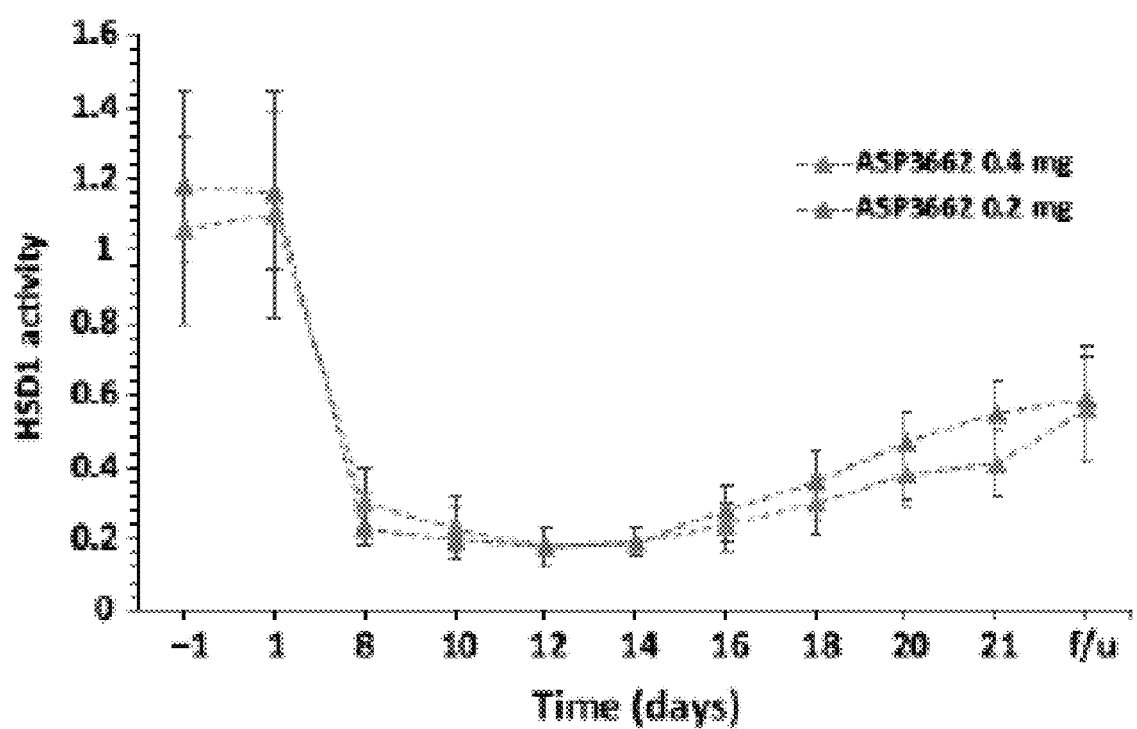
FIG. 2—Shows liver HSD-1 inhibition by SPI-62 (formerly ASP3662). Data shown are a unitless ratio of tetrahydrocortisols to tetrahydrocortisone in urine, a standard measure for liver HSD-1 activity. The last daily SPI-62 dose was administered on Day 14. The follow-up visit was on approximately Day 28.

Hepatic HSD-1 inhibition, assessed by the urinary HSD-1 ratio, is durable following cessation of SPI-62 dosing. In healthy adults, the return of the urinary HSD-1 ratio to baseline was incomplete for more than 2 weeks after the last dose. For example, at 16±2 days after cessation of daily doses of SPI-62 0.7 mg, the mean urinary HSD-1 ratio was 55% reduced from baseline, compared to 84% reduction from baseline on the last dosing day. Similar data were observed following both lower (FIG. 2) and higher daily doses of SPI-62. In patients with painful diabetic peripheral nephropathy administered daily doses of 10 mg SPI-62 for 6 weeks, the mean urinary HSD-1 ratio was 1.06 prior to dosing, 0.13 on the last dosing day, and 0.33 at 2 weeks after the last dose.

Figure 3:
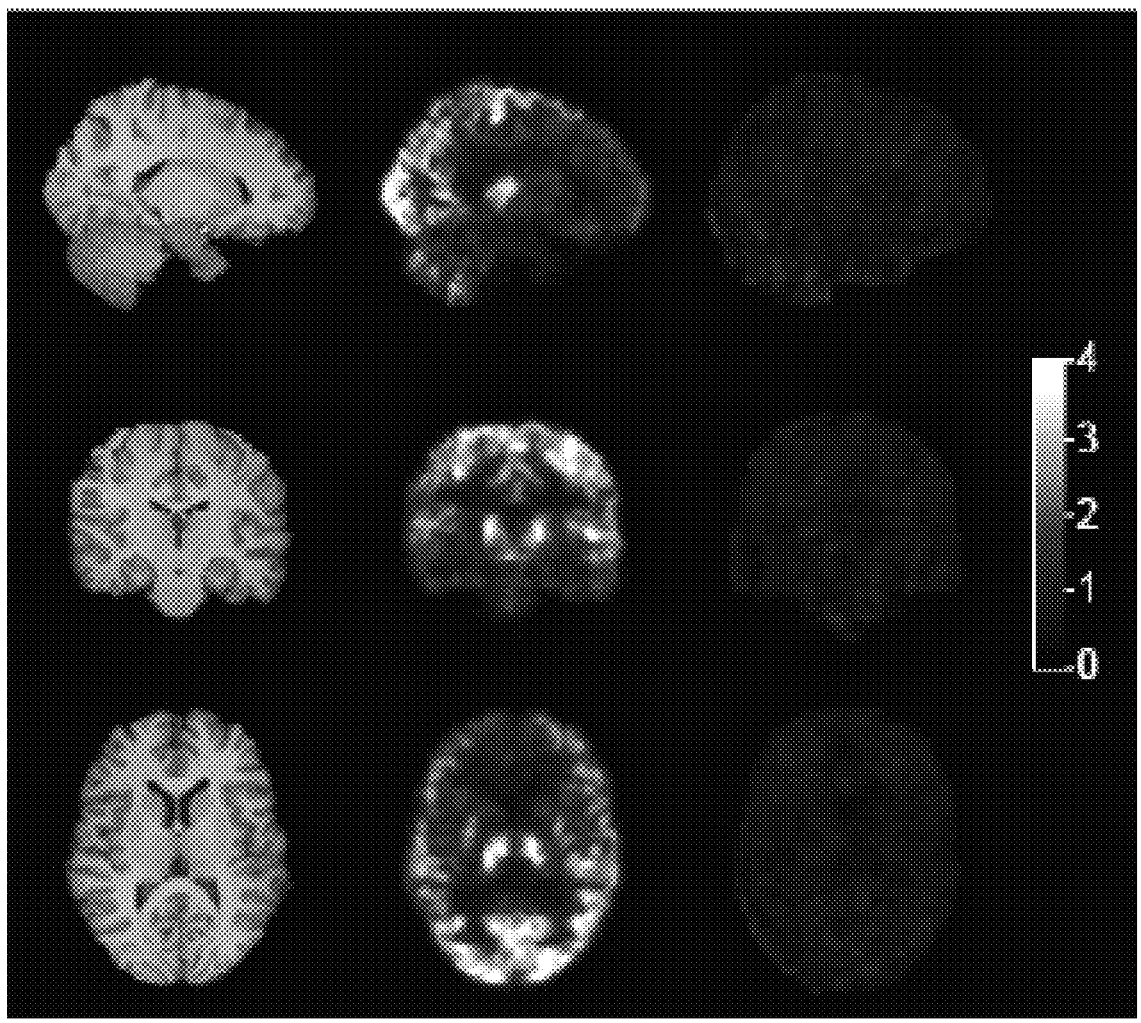
FIG. 3—Shows brain HSD-1 inhibition by SPI-62. Data shown are magnetic resonance (left) and positron emission (center, right) imaging of the same individual prior to (left, center) and after (right) a single SPI-62 dose.

Brain HSD-1 occupancy following a single dose of SPI-62 3 mg, assessed by competition with the HSD-1-specific PET ligand [$^{11}$C]AS2471907, was 84-90% at 3.3 to 25 hours, 56-83% at 42 to 46 hours, 36 to 45% at 139 hours, and 26% at 189 hours. The pharmacologic half-life of SPI-62 in brain is, as expected, shorter than that in liver. See FIG. 3.

The lowest SPI-62 dose administered clinically to date, 0.2 mg daily for 14 days, was associated with mean 87% reduction of the urinary HSD-1 ratio from baseline on the last dosing day when the mean maximum plasma drug concentration ($C_{max}$) was <1 ng/mL. That corresponds to an unbound concentration <0.25 nM which is well below the $K_i$ of 5.3 nM and the $IC_{50}$ of 17 nM of SPI-62 for human HSD-1. Across the dose range of SPI-62 of 0.2 to 50 mg, mean urinary HSD-1 ratios were between 0.09 to 0.17 in each dose group. The final urinary HSD-1 ratios were concentration-independent; corresponding $C_{max}$ means ranged from <1 to 835 ng/mL. A single dose of SPI-62 1 mg was associated with mean 51% difference v placebo of the urinary HSD-1 ratio and a mean $C_{max}$<0.05 ng/mL (unbound concentration <0.012 nM). Mean urinary HSD-1 ratios were between 0.11 to 0.18 after single doses of 6 to 60 mg SPI-62; corresponding $C_{max}$ means ranged from 28 to 595 ng/mL.

Figure 4:
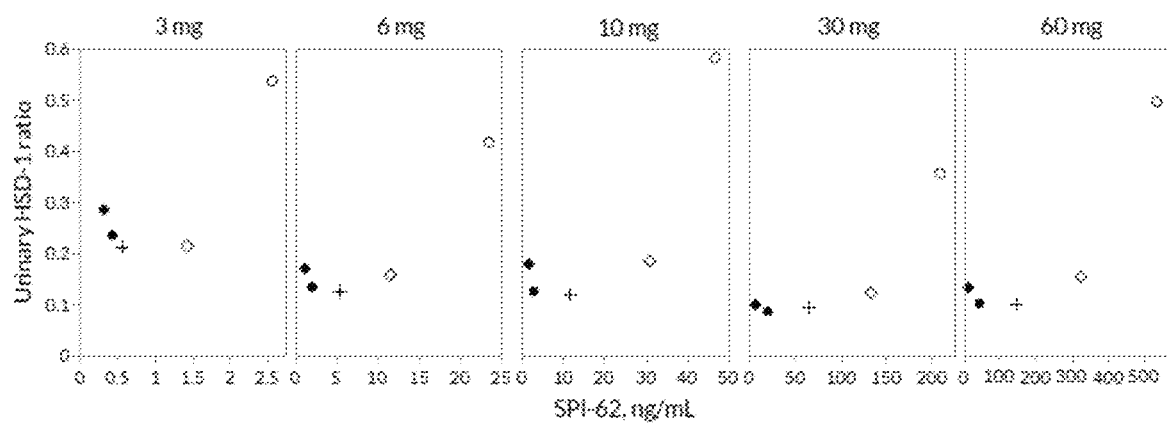
FIG. 4—Shows urinary HSD-1 ratios at dosages of 3 mg, 6 mg, 10 mg, 30 mg, and 60 mg. Urinary HSD-1 ratios were determined in urine collections 0 to 6 (o), 6 to 12 (O), 12 to 24 (+), 24 to 48 (e), and 48 to 72 (*) hours post-dose. Plasma SPI-62 levels are from the midpoint of each collection; those at 9 hours and 60 hours post-dose were interpolated from surrounding data. Mean values of six subjects per group are shown.

The expected hysteresis pattern was observed following administration of SPI-62 single doses. Urinary HSD-1 ratios were determined in urine collections 0 to 6 (o), 6 to 12 (0), 12 to 24 (●), 24 to 48 (♦), and 48 to 72 (4) hours post-dose (see FIG. 4). Plasma SPI-62 levels are from the midpoint of each collection; those at 9 hours and 60 hours post-dose were interpolated from surrounding data. Mean values of 6 subjects per group are shown.

During the first 6 hours after the dose, partial hepatic HSD-1 was observed without a monotonic concentration-response relationship. This is likely due to variability between groups in the duration of the initial distribution phase during which there would have been no or little HSD-1 inhibition. For intervals after that initial distribution phase, similar mean urinary HSD-1 ratios between 0.1 and 0.2 were associated with plasma drug levels from <2 to >300 ng/mL and across time intervals from 6 to 72 hours after the dose. A hysteresis plot is not shown for a single dose of SPI-62 1 mg dose as drug levels were all below the LLOQ (0.1 ng/mL). Mean urinary HSD-1 ratios after a 1 mg dose were 0.694, 0.471, 0.472, 0.522 and 0.618, each indicating partial hepatic HSD-1 inhibition, in urine collections 0 to 6, 6 to 12, 12 to 24, 24 to 48, and 48 to 72 hours post-dose.

ABT-384 has also been reported to show prolonged HSD-1 inhibition in vivo. Similar liver HSD-1 inhibition was measured in healthy adults after 7 daily doses of ABT-384 1 to 100 mg, with corresponding mean $C_{max}$ of 9.4 to 647 ng/mL. Complete brain HSD-1 inhibition was observed up to 40 hours after cessation of daily ABT-384 administration to healthy adults in a Phase 1 clinical trial.

The expected hysteresis pattern was observed following administration of a single oral dose of AMG-221 3 mg. Those data add confidence that AMG-221 is a pseudo-irreversible HSD-1 inhibitor.

Example 4. Pseudo-Irreversible HSD-1 Inhibitors Identified by In Vitro Enzyme Kinetics Pseudo-irreversible HSD-1 inhibitors can be identified via in vitro enzyme kinetics evaluation, in which they are expected to show longer enzyme residence times compared to other HSD-1 inhibitors. Surface plasmon resonance (SPR) is the resonant oscillation of conduction electrons at the interface between negative and positive permittivity material stimulated by incident light. When a protein is bound to a surface, SPR can be used to detect ligand binding to the protein.

Previously, it was reported that in vitro ABT-384 quickly forms a tight enzyme-inhibitor complex with the HSD-1 enzyme but has a very slow dissociation rate.

The binding affinity and kinetics of 19 HSD-1 inhibitors were characterized using SPR. Each compound was tested by A-B-A method using parallel experimental design in 50 mM Tris, 150 mM NaCl, 2% DMSO, pH7.4 at 30 L/min flow rate. Enzyme was exposed to 300 µM NADPH in 50 mM Tris, 150 mM NaCl, 2% DMSO, pH7.4 for 90 seconds (A step), then 300 µM NADPH and test compound in buffer for 150 seconds (B step), then 300 M NADPH in buffer for 300 to 370 seconds (A step). Association and dissociation of test compounds were monitored in the presence of 300 M NADPH throughout the experiment. Four concentrations of test compounds were prepared by two-fold serial dilution in 50 mM Tris, 150 mM NaCl, 2% DMSO, pH7.4 with 300 M NADPH. The residence time (reciprocal of the dissociation rate constant) for each compound is shown below in Table 1.

TABLE 1

Residence Time for HSD-1 Inhibitors

| Compound | Residence Time (s) |
|---|---|
| ABT-384 | 2611 |
| BI-187004 | 758 |
| UE-2343 | 543 |
| SPI-62 | 535 |
| KR-67607 | 518 |
| ABT-384 acid metabolite | 422 |
| SPI-09 | 342 |
| PF915275 | 304 |
| INCB-13739 | 272 |
| AMG-331 | 249 |
| BI-135585 | 222 |
| AZD4017 | 217 |
| AZD8329 | 207 |
| MK-0916 | 195 |
| SPI-09 stereoisomer | 192 |
| BMS-770767 | 184 |
| BMS-816336 | 129 |
| BMS-823778 | 122 |
| BVT-2733 | 65 |

Based on these results, ABT-384, BI-187004, UE-2343, SPI-62, and KR-67607 are identified as probable pseudo-irreversible HSD-1 inhibitors.

The rationale to so classify only those is as follows.

Although no clinical pharmacokinetic or pharmacodynamic data have been published for KR-67607, it had an enzyme residence time very similar to SPI-62, which is also established as a pseudo-irreversible HSD-1 inhibitor by clinical pharmacokinetic and pharmacodynamic results. KR-67607 also shares important chemophores with ABT-384, another established pseudo-irreversible HSD-1 inhibitor and appears to share a binding mode to human HSD-1 with both SPI-62 and ABT-384 (see below).

ABT-384 acid metabolite is only 19% as potent an HSD-1 inhibitor in vitro as ABT-384. Further, there is structural basis to consider that ABT-384 acid metabolite is not a pseudo-irreversible HSD-1 inhibitor.

SPI-09 showed dose-proportional pharmacokinetics in cynomolgus monkey across a wide range of single doses which would not be expected for a pseudo-irreversible HSD-inhibitor. Pharmacokinetic behavior of ABT-384 in cynomolgus monkey was similar as in human. A Pro-Cys motif important for allosteric regulation of human HSD-1 (see below) is shared by cynomolgus monkey, further supporting it as an appropriate species in which to characterize pseudo-irreversible HSD-1 inhibitors.

Accordingly, ABT-384 acid metabolite, SPI-09, and other HSD-1 inhibitors with shorter enzyme residence times are not classified as pseudo-irreversible inhibitors by in vitro enzyme kinetics.

The inhibitors that showed tachyphylaxis on adipose HSD-1 inhibition (BI-135585, AZD4017, AZD8329) are not classified as pseudo-irreversible inhibitors by in vitro enzyme kinetics.

However, some compounds (MK-0916, BMS-823778) that show clinical pharmacokinetics consistent with pseudo-irreversible inhibition are not so classified by in vitro enzyme kinetics. A possible limitation of SPR is that the allosteric conformation of human HSD-1 in vivo (see below) is not maintained under experimental conditions. To the extent that the binding mode(s) of pseudo-irreversible HSD-1 inhibitors depend(s) on the enzyme's native allosteric conformation, SPR might show long residences times for only some pseudo-irreversible HSD-1 inhibitors. BMS-823778 has a different binding mode to human HSD-1 compared to SPI-62, ABT-384, and KR-67607 (see below). MK-0916 has chemical structure similarities to BMS-823778; those two molecules might bind similarly to human HSD-1.

Figure 5:
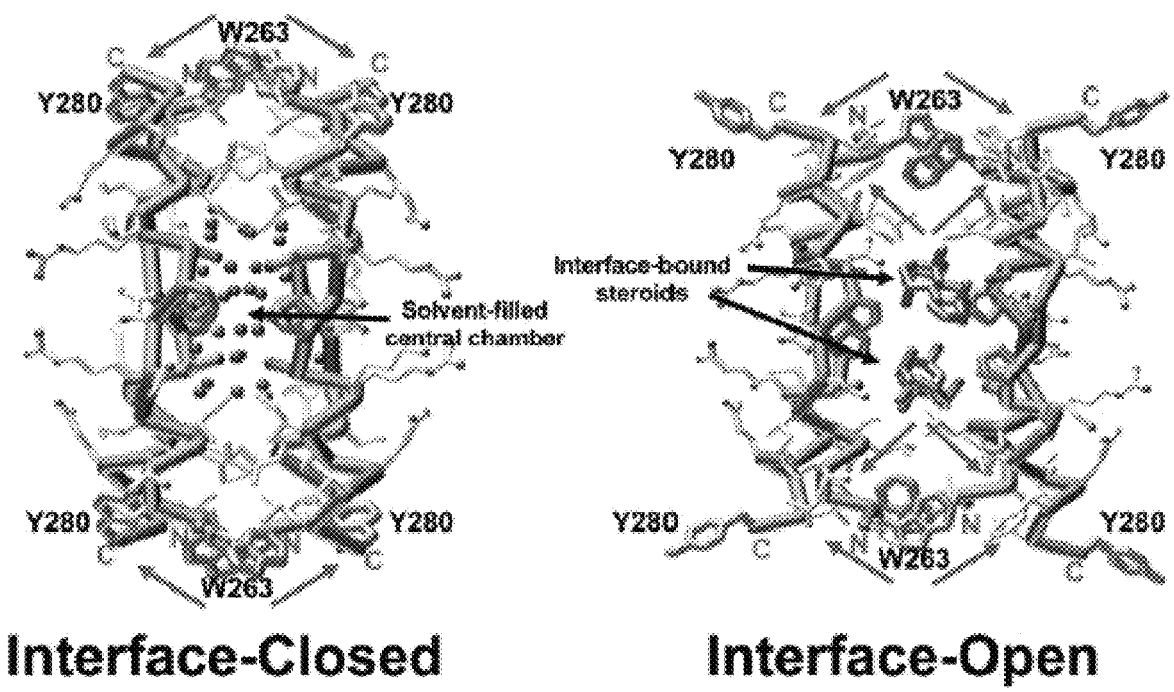
FIG. 5—Shows the glucocorticoid (steroid) binding dependence of the HSD-1 tetramer conformation.

Example 5. Pseudo-Irreversible HSD-1 Inhibitors Identified by Enzyme-Inhibitor Structure Human HSD-1 appears to function as a tetramer. A primate-specific C-terminal proline (P) 271-cysteine (C) 272 motif is localized at the center of the tetramer and forms reversible enzyme disulfides that alter enzyme activity. Conformational flexibility at the tetramerization interface is coupled to structural changes at the enzyme active site suggesting that the central P271-C272 motif may regulate enzyme activity. Two dimers associate through complementary interactions between pairs of enzyme carboxyl termini that are oriented in an antiparallel direction. Each carboxyl terminus in the HSD-1 tetramer runs roughly perpendicular to the dimer 2-fold axis. This arrangement of termini generates a 30-Å long 4-helix bundle-like structure that localizes adjacent enzyme active sites to the top and bottom of the structure (FIG. 5). Substrate (e.g., cortisone) binding induces a conformational shift of the tetramer to provide enzyme specificity and protect the active site from bulk transfer to promote hydride transfer.

Figure 6:
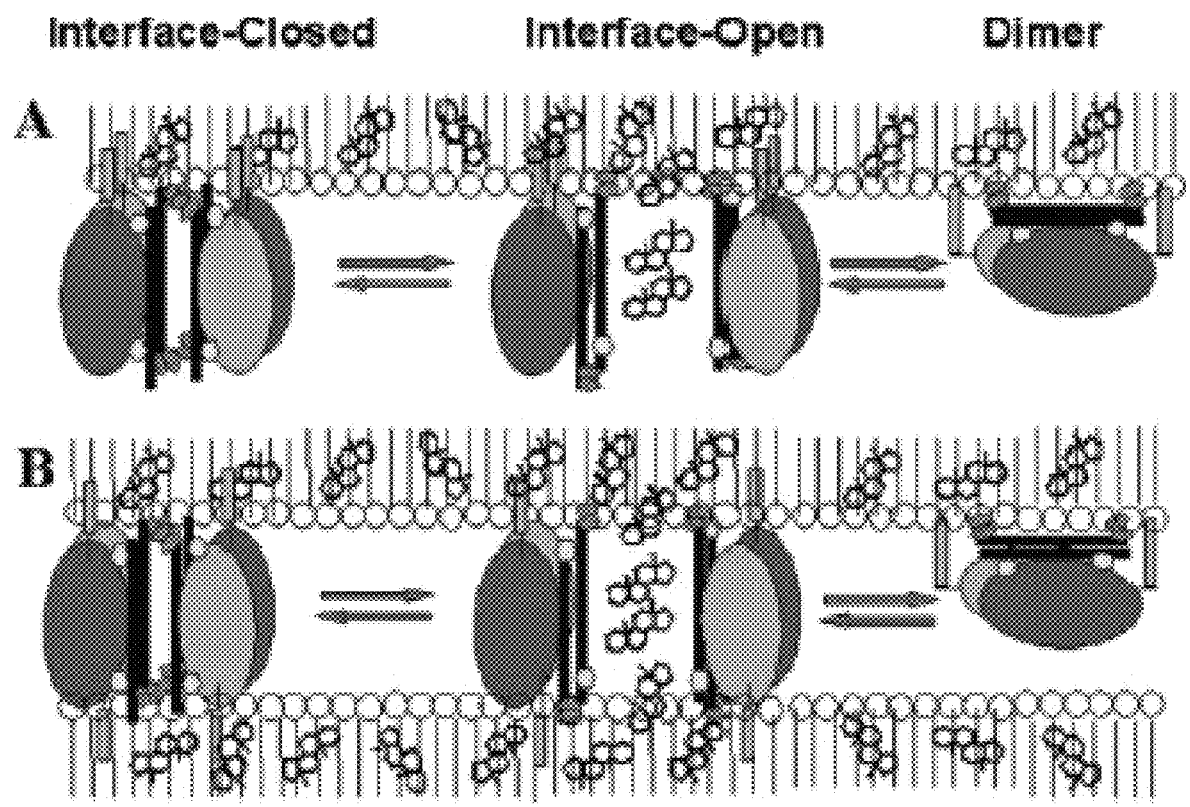
FIG. 6—Shows models for HSD-1 tetramers in the endoplasmic reticulum.

Two structure-based models for HSD-1 membrane interaction and subunit assembly in the endoplasmic reticulum lumen have been proposed (FIG. 6). The highly invaginated membrane structure of the endoplasmic reticulum is consistent with the model in which a tetramer that spans two lipid bilayers forms a chamber in which a pseudo-irreversible inhibitor, after slow dissociation from HSD-1, could rapidly re-associate to HSD-1 within the same tetramer to achieve long-lasting inhibition.

HSD-1 belongs to the short-chain dehydrogenase/reductase (SDR) enzyme family, which have a common reaction mechanism in which an active site tyrosine (Y) functions as a catalytic acid to protonate the reactive keto oxygen of the bound substrate. An active site serine (S) stabilizes the orientation of the bound substrate. A conserved lysine (K) forms hydrogen bonds with the nicotinamide ribose of NADPH and lowers the $pK_a$ of the Y hydroxyl to promote proton transfer. In HSD-1, the catalytic triad is S170-Y183-K187. Many HSD-1 inhibitors interact with the catalytic triad, particularly S170 and Y183. Some HSD-1 inhibitors interact instead with the alpha-helical backbone near the catalytic triad.

It was hypothesized that formation of a ternary complex with HSD-1 protein and NADPH cofactor is a common characteristic of pseudo-irreversible inhibitors. Among 39 HSD-1 inhibitors for which structures bound to HSD-1 have been deposited to the Protein Data Bank, a minority appear to form such ternary complexes directly with NADPH. Those can be further classified according to 3 types of interactions: (1) Hydrogen bonds between an amide nitrogen and NADPH pyrophosphate (Amide); (2) Hydrogen bonds between an aromatic nitrogen and NADPH pyrophosphate (Aromatic); and (3) An aromatic stacking interaction with NADPH nicotinamide ring (Stack). Interactions with the catalytic triad and nearby backbone are also summarized in Table 2 below.

TABLE 2

Interactions with Catalytic Triad and Backbone

| Inhibitor | PDB Record | NADP(H) | S170 | Y183 | K187 | Backbone |
|---|---|---|---|---|---|---|
| Compound A | 2irw | Amide | Yes | Yes | No | No |
| SAR184841 | 4hx5 | Amide | Yes | Yes | No | No |
| Compound B | 3qqp | Aromatic | Yes | Yes | No | No |
| Compound C | 2rbe | Stack | Yes | Yes | No | No |
| Compound D | 3oq1 | Stack | No | No | No | Yes |
| BMS-823778 | 5qii | Stack | Yes | Yes | No | No |

Association of one of these drugs to HSD-1 would be a bimolecular reaction, whereas dissociation would be a process in which interactions of both the drug and the catalytic cofactor NADPH to HSD-1 contribute to the activation energy barrier to dissociation. In a sense, the binding energy of NADPH to HSD-1 would also hold the inhibitor to HSD-1. This results in the fast-on, slow-off kinetics characteristic of pseudo-irreversible inhibitors.

The other 33 inhibitors for which structures bound to HSD-1 are available, including AZD4017 (PDB record 4hfr) and AZD8329 (PDB record 4p38), both of which show tachyphylaxis on adipose HSD-1 inhibition, do not form ternary complexes that include NADPH or do so only via water molecules. Water molecules might be sufficiently mobile in the active site such that complexes between an HSD-1 inhibitor and NADPH in the human HSD-1 active site via water molecules cannot presently be predicted to confer the same advantages as Amide, Aromatic, and Stack interactions.

Figure 7:
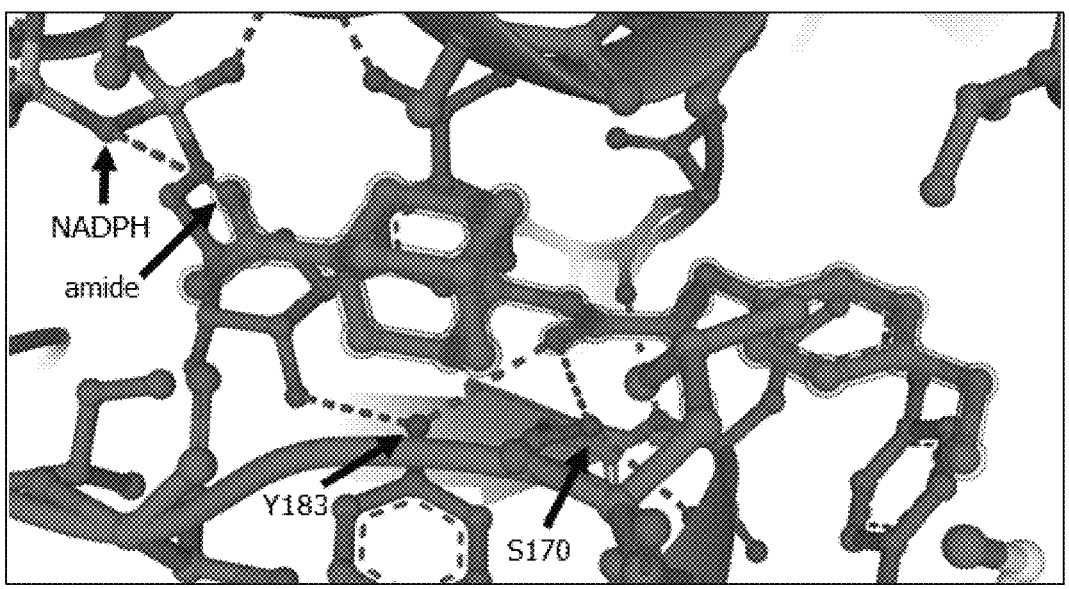
FIG. 7—Shows the structure of Compound A bound to human HSD-1 (PDB record 2irw) showing the Amide class of ternary complex with NADPH in the active site.
Figure 8:
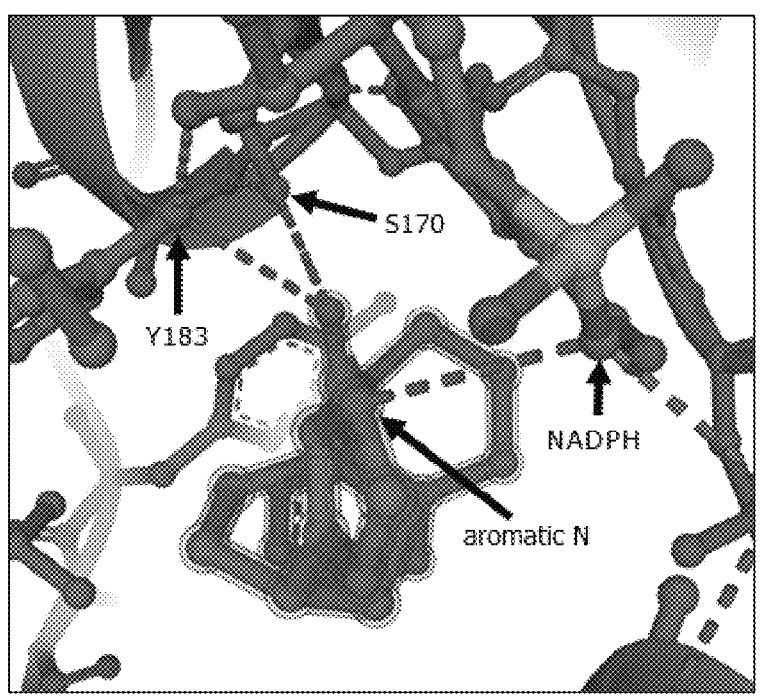
FIG. 8—Shows the structure of Compound B bound to human HSD-1 (PDB record 3qqp) showing the Aromatic class of ternary complex with NADPH in the active site.

Compound A [(1s,3R,5S,7s)-4-(2-(4-methoxyphenoxy)-2-methylpropanamido)adamantane-1-carboxamide)], shown in FIG. 7, is useful because the portions of the molecule that interact with NADPH and the catalytic triad are identical to those in ABT-384 and KR-67607. Using molecular docking techniques, modeling of the binding of SPI-62, ABT-384, and KR-67607 to HSD-1 was performed. The models show that these inhibitors plausibly form ternary complexes of the Amide class with NADPH in the active site. They, along with SAR-184841 and Compound A are classified as pseudo-irreversible HSD-1 inhibitors.

Figure 10:
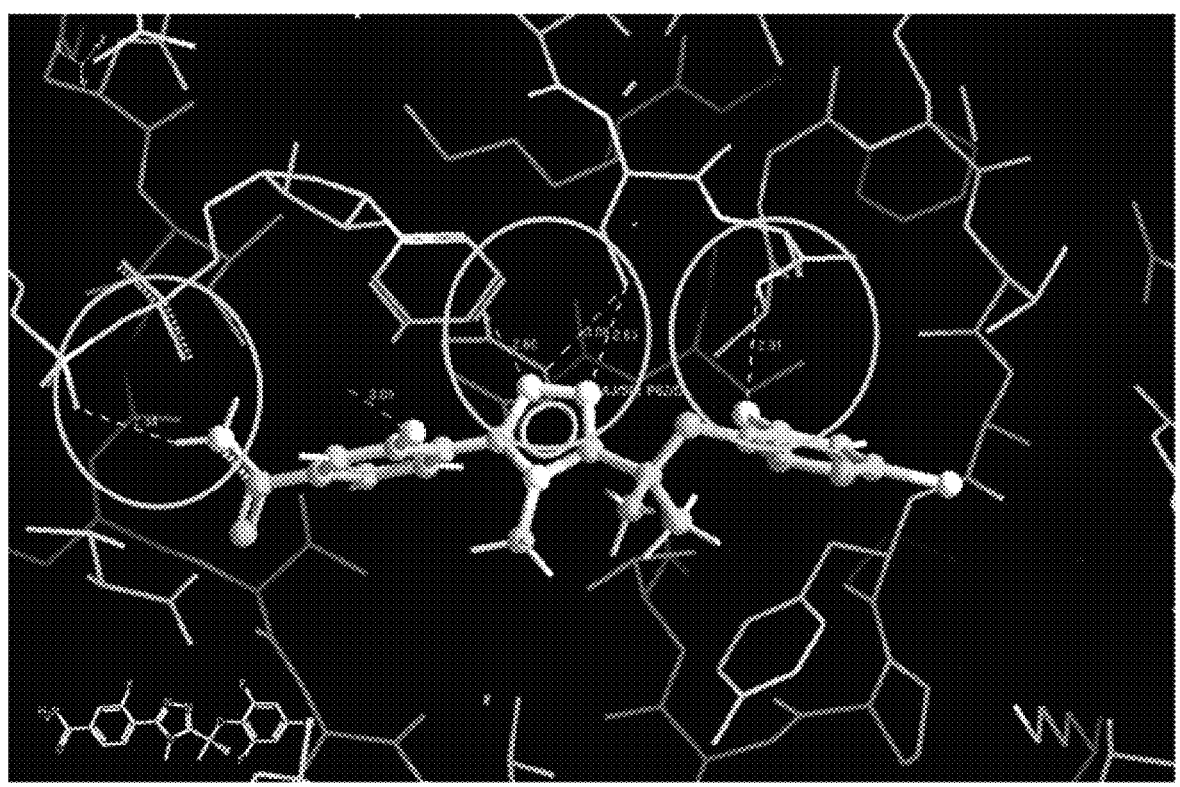
FIG. 10—Shows a molecular docking model of SPI-62 and its interactions with pyrophosphate (left), serine (S) 170/tyrosine (Y) 183 (center), and alanine (A) 172 main chain (right of center), which show that it forms an Amide class ternary complex with NADPH in the HSD-1 active site.

SPI-62 shows distinct but similar interactions compared to other class members. For example, (a) Benzamide, rather than adamantane carboxamide, interaction with NADPH pyrophosphate; and (b) Triazine ring, rather than amide keto, interaction with S170 and Y183 (FIG. 10). BMS-823778 and other HSD-1 inhibitors also show such triazine interactions with S170 and Y183.

Molecular docking models of the acid metabolites of SPI-62 and ABT-384 suggest that the metabolites bind in an opposite orientation with the benzoic acid or adamantane carboxylic acid pointed away from NADPH pyrophosphate. This is a structural basis for why the acid metabolites are substantially less potent HSD-1 inhibitors compared to the parent drugs.

Figure 9:
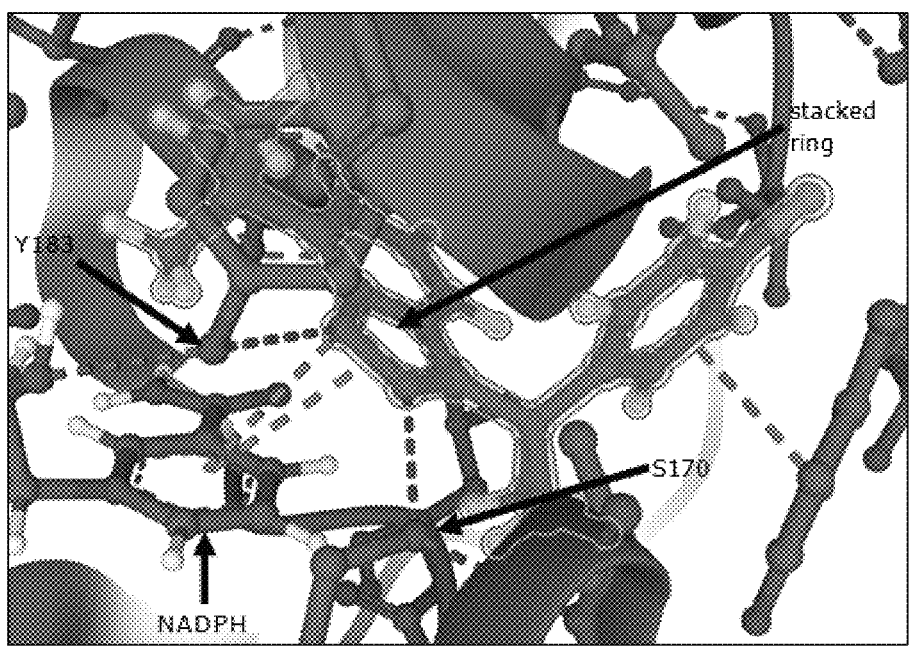
FIG. 9—Shows the structure of BMS-823778 bound to human HSD-1 (PDB record 5qii) showing the Stack class of ternary complex with NAPDH in the active site.

The triazine rings of MK-0916 and BMS-823778 interact with the nicotinamide ring of NADPH, S170, and Y183, a structural basis for them as pseudo-irreversible HSD-1 inhibitors. FIG. 9 shows the established binding of BMS-823778. Using molecular docking techniques, modeling of the binding of MK-0916 was performed to determine if the binding mode is similar to that of BMS-823778. The model showed that this inhibitor plausibly forms a ternary complex of the Stack class with NADPH in the active site. Compound C and Compound D (PDB records 2rbe and 3oq1, Table 2) may also be pseudo-irreversible HSD-1 inhibitors. Compounds which form Aromatic class ternary complexes with NAPDH in the HSD-1 active site (e.g., Compound B; PDB record 3qqp) could be pseudo-irreversible inhibitors.

Example 6. Evidence for HSD-1 Inhibitors as Potential Treatments for Glucocorticoid Excess The therapeutic hypothesis for HSD-1 inhibitors for patients with glucocorticoid excess, whether endogenous (Cushing's syndrome and ACS) or exogenous (GC medications) is that HSD-1 forms much of the excess intracellular GC that can bind to intracellular GC and mineralocorticoid receptors, as well as non-genomic receptors, and thereby cause symptoms. HSD-1 inhibition can diminish that intracellular GC and so has potential to diminish symptoms in patients with Cushing's syndrome or ACS. It may also prevent or reverse many of the adverse effects associated with GC medication use, particularly in patients who rely on long-term use of GC medicines to control autoimmune diseases and other conditions.

Several lines of independent clinical and non-clinical evidence support the potential of HSD-1 inhibitors for the treatment of Cushing's syndrome or ACS, or as adjunctive therapy to GC in patients in need of such medications.

HSD-1 activity is elevated in patients with Cushing's syndrome. The urinary HSD-1 ratio, a biomarker for hepatic HSD-1 activity, was 1.74±0.24 in patients with Cushing's disease, 3.95±0.69 in patients with ectopic ACTH secretion, and 1.7 (median) in patients with adrenal Cushing's syndrome, in contrast to 1.21±0.06 in healthy adults. The elevated HSD-1 ratios are considered a consequence of HSD-1 induction by cortisol.

Patients with Cushing's syndrome and constitutionally low HSD-1 activity showed no hypercortisolism-related symptoms despite very high 24-hour urinary free cortisol. For example, a 20-year-old female presented with amenorrhea, an androgenic symptom of Cushing's, and showed no sequelae of hypercortisolism. Her urinary free cortisol was 831 and 1049 nmol/24 hr on separate occasions and her urinary HSD-1 ratio was 0.66. Following transsphenoidal adenomectomy, she began to menstruate, and her circulating and urinary cortisol levels returned to normal. In another example, a 55-year-old female presented with an incidentally discovered adrenal tumor. She showed no physical signs of Cushing's syndrome, insulin resistance, hypertension, or dyslipidemia. Her urinary free cortisol was 1149 nmol/24 hr and her urinary HSD-1 ratio was 0.61 to 0.66 on separate occasions. Following adrenalectomy, high dose glucocorticoid therapy was initially required to prevent adrenal insufficiency.

A pilot open-label clinical trial of an HSD-1 inhibitor (S-707106) in patients with hypercortisolism (11 with ACS, 4 with Cushing's syndrome) showed positive trends on glycemic control and body habitus. At 24 weeks, subjects showed on average 1.6 kg bodyweight loss, 2.5% decrease of body fat percentage, and 2.4% increase of body muscle percentage. Glucose area under the curve following oral glucose tolerance test decreased predominantly in obese subjects.

In a cohort of healthy adult males, those administered prednisolone 20 mg for 7 days together with an HSD-1 inhibitor (AZD4017) showed resistance to insulin sensitivity decrease during a euglycemic clamp, triglycerides increase, nighttime blood pressure increase, bone formation biomarker decrease, and bone resorption biomarker increase, compared to those administered prednisolone only.

Clinical trial results with various HSD-1 inhibitors support efficacy for treatment of certain common chronic diseases and disorders that correspond to morbidities of GC excess, including INCB-13739 for diabetes, R05093151 for non-alcoholic fatty liver disease, and AZD4017 for impaired wound healing. HSD-1 inhibitors in some clinical trials have also been associated with 1-2 kg weight loss at 12 weeks compared to placebo. Other clinical trials of HSD-1 inhibitors have shown lack of efficacy even with administration of an adequate dose and positive results for an active control, such as ABT-384 for dementia. Yet other clinical trials of HSD-1 inhibitors have shown lack of efficacy, possibly for reasons such an insufficient treatment period or exclusion of patients with GC excess, for example BI-187004 for diabetes. Diabetes, non-alcoholic fatty liver disease, impaired wound healing, obesity, and dementia are complex conditions for which cortisol excess is only one of multiple etiologic factors and not in all patients. HSD-1 inhibitors might be expected to be particularly beneficial for patients with GC excess for whom such treatment is targeted specifically to a major cause of the morbidity they suffer. This could be the situation even for morbidities (e.g., cognitive impairment) in which prior HSD-1 inhibitor clinical trials have been negative.

HSD-1 knockout mice resist multiple adverse effects of exogenously administered corticosterone (CORT; the murine equivalent of cortisol). CORT suppressed HPA axis activity, as evidenced by adrenal atrophy, similarly in both knockout and control mice. In contrast to control mice, the knockout mice showed essentially no effect of corticosterone on blood pressure and hepatic steatosis, and substantially reduced effects of CORT on insulin resistance, adiposity, muscle wasting, and dermal atrophy. The knockout mice almost fully resisted the adverse effects of CORT on trabecular bone structure.

HSD-1 inhibitors have demonstrated ability to block or reverse exogenously administered GC in animal models. An Abbott HSD-1 inhibitor blocked the adverse reactions of GC administration on bone in rats. Femoral head necrosis induced by the mycotoxin patulin and prednisolone was improved by administration of an HSD-1 inhibitor, demonstrating improvement in bone microstructure and density. Carbenoxolone and PF-915275 each prevented GC-induced wound healing impairment in mouse. Glycyrrhizin partially prevented intraocular pressure increase associated with intravitreal triamcinolone in rabbit.

Example 7. Supportive Evidence Specific to SPI-62

Clinical and non-clinical evidence support the specific potential of SPI-62 for the treatment of Cushing's syndrome or ACS, or as adjunctive therapy to GC in patients in need of such medications.

Analyses of covariance were conducted to analyze total cholesterol (TC), glucose, glycated hemoglobin (HbA1c), and triglycerides (TG), with baseline value as the covariate and a baseline*treatment interaction term, in patients with painful diabetic peripheral neuropathy following daily administration of SPI-62 or placebo. Data were obtained from study 3662-CL-0049, a Phase 2 randomized, double-blind, placebo- and active-controlled clinical trial of the safety and efficacy of SPI-62 in subjects with painful diabetic peripheral neuropathy.

Figure 11:
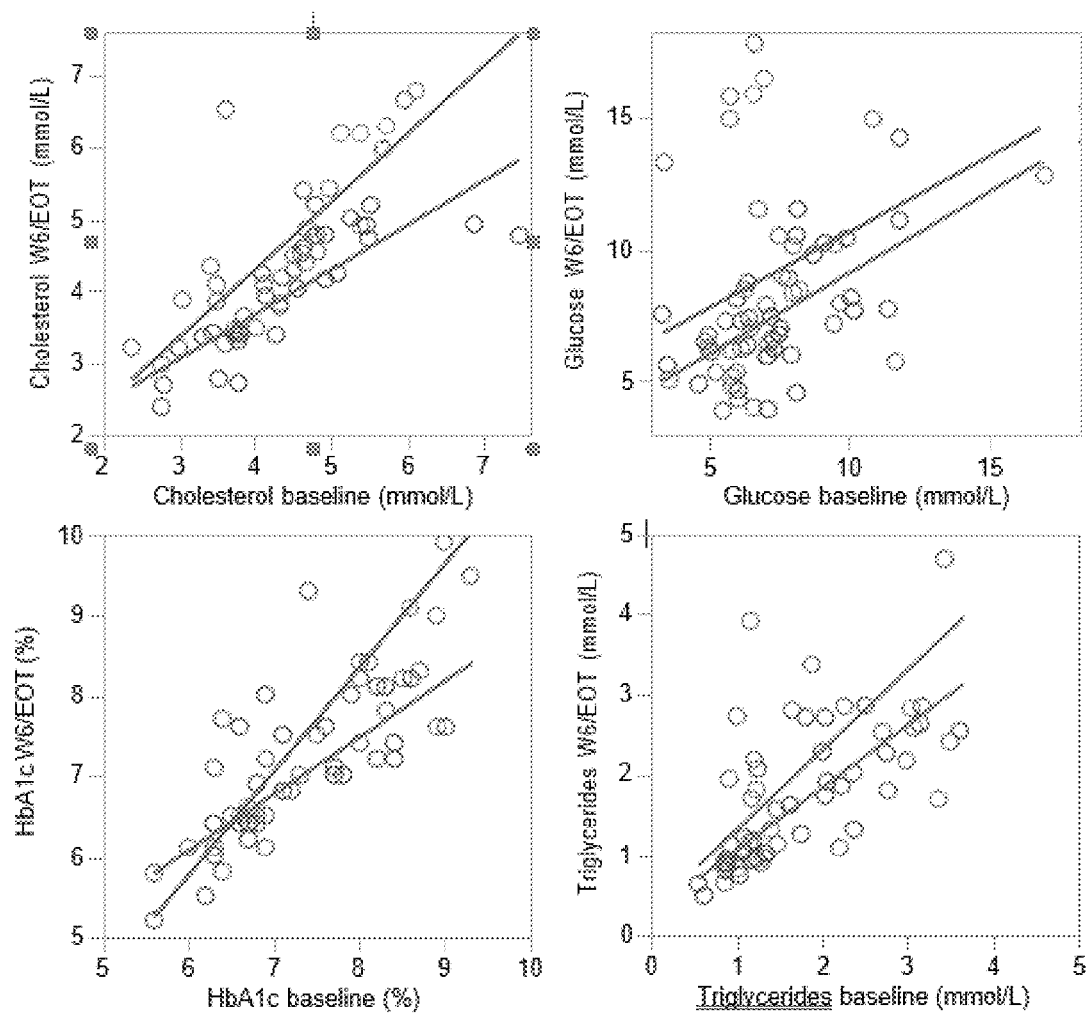
FIG. 11—Shows the interaction of baseline parameter values with treatment at Week 6/end of trial (EOT) in human subjects with painful diabetic peripheral neuropathy. Green circles and regression lines are SPI-62; grey circles and regression lines are placebo.

SPI-62 was associated with lower baseline-adjusted values, compared to placebo, on TC, glucose, HbA1c, and TG at Week 6/end-of-trial (EOT). The magnitude of difference decreased during 2 weeks after cessation of study drug administration (Week 8/end-of-study (EOS)) on TC, glucose, and TG, but increased on HbA1c. Treatment*baseline interactions were observed on TC and HbA1c at Week 6/EOT, such that patients with higher baseline values showed on average larger differences between SPI-62 and placebo, but not on glucose or TG (FIG. 11). Thus, overall, SPI-62 was associated with favorable changes on TC, glucose, HbA1c, and TG in patients with PDPN. These analyses increase confidence that SPI-62 has potential to control hyperglycemia and dyslipidemia. Patients with higher TC or HbA1c values might particularly benefit from SPI-62 therapy.

The magnitudes of effect of SPI-62, a pseudo-irreversible HSD-1 inhibitor, on HbA1c, TC, and TG (Table 3) were numerically larger than those reported for other HSD-1 inhibitors in other clinical trials.

TABLE 3

Effects of HSD-1 Inhibitors on HbA1c, TC, and TG.

| Parameter (unit) | Least squares mean (standard error) N = 36 per arm | | | |
|---|---|---|---|---|
| | Week 6/EOT | | Week 8/EOS | |
| | SPI-62 | Placebo | SPI-62 | Placebo |
| TC (mmol/L) | 3.95 (0.120) | 4.71 (0.111) | 4.16 (0.105) | 4.53 (0.107) |
| Glucose (mmol/L) | 7.61 (0.556) | 9.25 (0.524) | 7.78 (0.546) | 8.90 (0.546) |
| HbA1c (mmol/L) | 7.10 (0.186) | 7.60 (0.171) | 7.02 (0.162) | 7.64 (0.164) |
| TG (mmol/L) | 1.68 (0.202) | 2.10 (0.186) | 1.63 (0.113) | 1.90 (0.115) |

To demonstrate mitigation by SPI-62 of corticosterone (CORT) adverse effects in mouse, C57BL/6 male mice (age 7 weeks; n=14 per group) were administered CORT (100 mg/mL in drinking water) and SPI-62 (by gavage in 0.5% HPMC; 0, 1, or 10 mg/kg/day or 10 mg/kg twice daily) for 35 days. A control group received no CORT or SPI-62. Body weight was assessed daily and food consumption twice weekly. Whole body muscle and fat amounts were measured at Days 0, 14, and 28 using an EchoMRI-130H body composition analyzer. Blood samples for fasting glucose and insulin were obtained at Days 1 (pre-dose), 15, 29, and 35. An open field test was conducted on Day 22. A grip strength test was performed on Day 28. After sacrifice on Day 36, gonadal, subcutaneous, retroperitoneal, and mesenteric fat, quadriceps, and tibialis anterior were dissected and weighed, and skin was formalin fixed and paraffin embedded.

Figure 12:
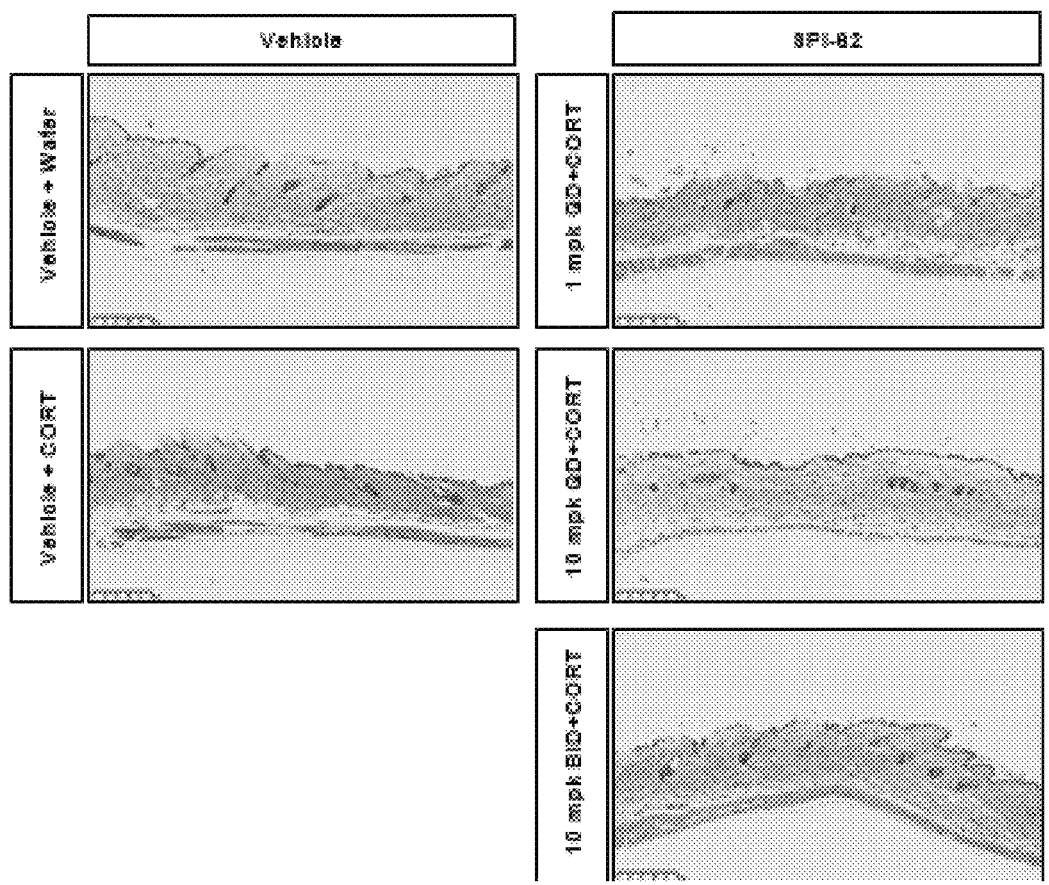
FIG. 12—Shows representative mouse dermal cross sections after 35 days treatment with corticosterone (CORT) in drinking water and SPI-62 or vehicle by gavage.
Figure 13:
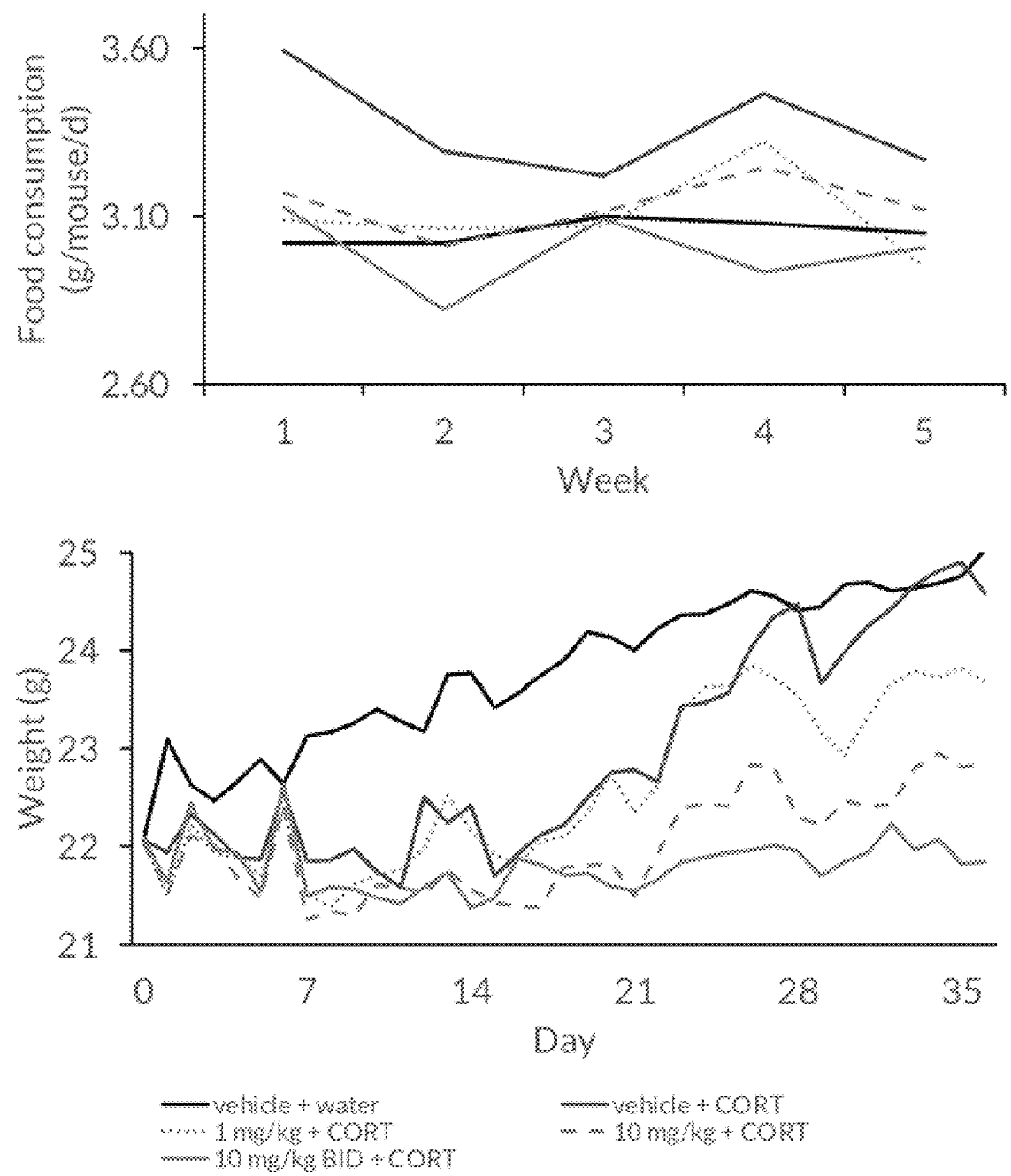
FIG. 13—Shows food consumption and weight statistics for mice that received corticosterone (CORT) in drinking water and SPI-62 or vehicle by gavage for 5 weeks. Food consumption was measured twice weekly; weekly means are shown. Weight was measured daily; means are shown.

CORT resulted in increased food consumption, which appeared to be normalized by SPI-62. CORT-treated mice showed reduced body weight gain for 2 weeks then accelerated body weight gain. SPI-62 prevented body weight gain acceleration. CORT effects on dermal thickness and structure were less prominent in mice who also received SPI-62. No effect of CORT or SPI-62 was observed in the open field test. SPI-62 prevented CORT adverse effects of insulin resistance, increased adiposity, skeletal myoatrophy, and grip strength reduction. SPI-62 prevented several CORT adverse effects in mouse, demonstrating that blockade of local intracellular glucocorticoid activation by an HSD-1 inhibitor in target tissues can mitigate glucocorticoid toxicity. See Tables 4 through 9 and FIGS. 12 and 13.

TABLE 4

Insulin resistance in mice administered CORT and SPI-62 Mice (n = 14 per group received corticosterone in drinking water and SPI-62 or vehicle by gavage for 35 days. Data were analyzed by ANCOVA with baseline as the covariate.

| | HOMA-IR (mmol glucose/µU insulin) | | | | | |
|---|---|---|---|---|---|---|
| | Day 15 | | Day 29 | | Day 35 | |
| Group | LSM | SE | LSM | SE | LSM | SE |
| Vehicle + Water | 0.78 | 0.46 | 0.73 | 0.37 | 1.02 | 3.86 |
| Vehicle + CORT | 4.02$^a$ | 0.47 | 5.71$^a$ | 0.38 | 23.71$^a$ | 4.01 |
| 1 mg/kg QD + CORT | 3.73$^a$ | 0.44 | 3.56$^{ab}$ | 0.35 | 8.16$^b$ | 3.73 |
| 10 mg/kg QD + CORT | 1.41$^b$ | 0.44 | 1.88$^{ab}$ | 0.35 | 2.28$^b$ | 3.72 |
| 10 mg/kg BID + CORT | 0.94$^b$ | 0.44 | 0.94$^b$ | 0.36 | 2.16$^b$ | 3.74 |

$^a$P < 0.05 v Vehicle + Water;
$^b$P < 0.05 v Vehicle + CORT

TABLE 5

Whole-body muscle and fat content in mice administered CORT and SPI-62 Mice (n = 14 per group received corticosterone in drinking water and SPI-62 or vehicle by gavage for 35 days. Data were analyzed by ANCOVA with baseline as the covariate.

| | | Day 14 | | Day 28 | |
|---|---|---|---|---|---|
| | Group | LSM | SE | LSM | SE |
| Muscle content | Vehicle + Water | 0.88 | 0.02 | 0.84 | 0.02 |
| | Vehicle + CORT | 0.80$^a$ | 0.02 | 0.71$^a$ | 0.02 |
| | 1 mg/kg QD + CORT | 0.82$^a$ | 0.02 | 0.77$^a$ | 0.02 |
| | 10 mg/kg QD + CORT | 0.87$^b$ | 0.02 | 0.80$^b$ | 0.02 |
| | 10 mg/kg BID + CORT | 0.89$^b$ | 0.02 | 0.86$^b$ | 0.02 |
| Fat content | Vehicle + Water | 0.069 | 0.008 | 0.070 | 0.011 |
| | Vehicle + CORT | 0.141$^a$ | 0.008 | 0.187$^a$ | 0.012 |
| | 1 mg/kg QD + CORT | 0.121$^a$ | 0.008 | 0.142$^{ab}$ | 0.011 |
| | 10 mg/kg QD + CORT | 0.061$^b$ | 0.008 | 0.115$^{ab}$ | 0.011 |
| | 10 mg/kg BID + CORT | 0.064$^b$ | 0.008 | 0.061$^b$ | 0.011 |

$^a$P < 0.05 v Vehicle + Water;
$^b$P < 0.05 v Vehicle + CORT

TABLE 6

Post-mortem (Day 36) fat depot weights in mice administered CORT and SPI-62 Mice (n = 14 per group) received corticosterone in drinking water and SPI-62 or vehicle by gavage for 35 days. Data were analyzed by ANOVA.

| Group | Fat depot weight (mg/g body weight) - Mean [SD] | | | |
|---|---|---|---|---|
| | Gonadal | Subcutaneous | Retroperitoneal | Mesenteric |
| Vehicle + Water | 6.08 [1.80] | 1.83 [0.69] | 1.76 [0.48] | 2.77 [0.70] |
| Vehicle + CORT | 15.23 [2.48]$^a$ | 10.44 [1.75]$^a$ | 5.77 [1.29]$^a$ | 9.42 [2.29]$^a$ |
| 1 mg/kg QD + CORT | 10.60 [2.28]$^{ab}$ | 4.04 [1.30]$^{ab}$ | 3.33 [1.21]$^{ab}$ | 6.46 [1.85]$^{ab}$ |
| 10 mg/kg QD + CORT | 8.44 [1.85]$^b$ | 3.35 [0.84]$^{ab}$ | 2.40 [0.40]$^b$ | 6.23 [1.30]$^{ab}$ |
| 10 mg/kg BID + CORT | 6.02 [1.33]$^b$ | 1.95 [0.65]$^b$ | 2.21 [0.61]$^b$ | 4.73 [0.88]$^{ab}$ |

$^a$P < 0.05 v Vehicle + Water;
$^b$P < 0.05 v Vehicle + CORT

TABLE 7

Post-mortem (Day 36) muscle weights in mice administered CORT and SPI-62 Mice (n = 14 per group) received corticosterone in drinking water and SPI-62 or vehicle by gavage for 35 days. Data were analyzed by ANOVA.

| Group | Muscle weight (mg/g body weight) - Mean [SD] | |
|---|---|---|
| | Quadriceps | Tibialis anterior |
| Vehicle + Water | 6.99 [1.14] | 2.25 [0.24] |
| Vehicle + CORT | 3.19 [0.86]$^a$ | 1.47 [0.30]$^a$ |
| 1 mg/kg QD + CORT | 3.98 [0.77]$^{ab}$ | 1.60 [0.18]$^a$ |
| 10 mg/kg QD + CORT | 5.33 [[0.70]$^{ab}$ | 2.14 [0.32]$^b$ |
| 10 mg/kg BID + CORT | 5.90 [0.83]$^{ab}$ | 2.36 [0.32]$^b$ |

$^a$P < 0.05 v Vehicle + Water;
$^b$P < 0.05 v Vehicle + CORT

TABLE 8

Observed group mean [standard deviation] food consumption in mice administered CORT and SPI-62. Mice (n = 7 co-housed pairs per group received corticosterone in drinking water and SPI-62 or vehicle by gavage for 35 days. Hypothesis testing was neither pre-specified nor conducted (see Methods).

| | Vehicle + Water | | Vehicle + CORT | | 1 mpk QD + CORT | | 10 mpk QD + CORT | | 10 mpk BID + CORT | |
|---|---|---|---|---|---|---|---|---|---|---|
| Day | Mean | SD | Mean | SD | Mean | SD | Mean | SD | Mean | SD |
| 4 | 2.99 | 0.42 | 3.75 | 0.35 | 3.26 | 0.24 | 3.37 | 0.42 | 3.36 | 0.32 |
| 8 | 3.05 | 0.21 | 3.43 | 0.53 | 2.92 | 0.20 | 2.98 | 0.27 | 2.88 | 0.21 |
| 11 | 3.12 | 0.27 | 3.30 | 0.37 | 3.09 | 0.25 | 3.11 | 0.32 | 2.92 | 0.25 |
| 15 | 2.92 | 0.34 | 3.28 | 0.36 | 3.04 | 0.33 | 2.91 | 0.20 | 2.74 | 0.22 |
| 18 | 3.13 | 0.26 | 3.19 | 0.34 | 2.91 | 0.30 | 3.08 | 0.18 | 3.36 | 0.43 |
| 22 | 3.06 | 0.28 | 3.25 | 0.35 | 3.23 | 0.37 | 3.15 | 0.33 | 2.89 | 0.28 |
| 25 | 3.24 | 0.19 | 3.61 | 0.22 | 3.74 | 0.36 | 3.50 | 0.19 | 3.13 | 0.30 |
| 29 | 2.92 | 0.23 | 3.32 | 0.21 | 2.90 | 0.18 | 2.99 | 0.34 | 2.79 | 0.29 |
| 32 | 3.10 | 0.20 | 3.26 | 0.32 | 2.77 | 0.37 | 3.00 | 0.62 | 3.27 | 0.60 |
| 36 | 3.00 | 0.29 | 3.28 | 0.30 | 3.13 | 0.17 | 3.24 | 0.12 | 2.83 | 0.30 |

TABLE 9

Observed group means and standard deviations of body weights at Baseline and at Days 15, 29, and 35 in mice administered CORT and SPI-62. Mice (n = 14 per group received corticosterone in drinking water and SPI-62 or vehicle by gavage for 35 days. Hypothesis testing was neither pre-specified nor conducted.

| Group | Baseline | | Day 15 | | Day 29 | | Day 35 | |
|---|---|---|---|---|---|---|---|---|
| | Mean | SD | Mean | SD | Mean | SD | Mean | SD |
| Vehicle + Water | 22.1 | 1.12 | 23.4 | 1.71 | 24.4 | 1.72 | 24.8 | 1.69 |
| Vehicle + CORT | 22.1 | 1.06 | 21.7 | 1.88 | 23.7 | 1.91 | 24.9 | 1.80 |
| 1 mpk QD + CORT | 22.1 | 1.04 | 21.9 | 2.00 | 23.2 | 2.80 | 23.8 | 2.96 |
| 10 mpk QD + CORT | 22.0 | 1.09 | 21.4 | 1.10 | 22.2 | 1.32 | 22.8 | 1.21 |
| 10 mpk BID + CORT | 22.1 | 1.29 | 21.5 | 1.29 | 21.7 | 1.51 | 21.8 | 1.50 |

Example 8. PK—AdiposePD Model Development

Male and non-menstruating female subjects with type 2 diabetes aged between 18 and 65 years with a body mass index between 30.0 and 45.0 were administered SPI-62 daily for 14 days. In addition to the six subjects described in Example 1 who received SPI-62 1, 3, or 6 mg for 14 days, six additional subjects received SPI-62 1, 2, 3, or 10 mg for 5 to 8 days. For at least 4 hours prior to, and throughout, selected dose intervals, D8 cortisone ([2,2,4,6,6,9,12,12-$^2H_8$] cortisone, Millipore Sigma, Miamisburg OH) 1 μg/mL in Perfusion Fluid T1 (M Dialysis, Stockholm Sweden)+0.5% alcohol USP was infused continuously into subcutaneous abdominal adipose tissue via microdialysis catheters (63 Microdialysis Catheter, MDialysis, Stockholm Sweden) at a rate of 1 L/min. Adipose dialysate was collected for two-hour intervals (0-2, 2-4, 4-6, 6-8, 8-10, 20-22, and 22-24 hours after the SPI-62 dose) and analyzed for D8 cortisone and D8 cortisol. The D8 cortisol mole percent fraction (MPF) was calculated as: ([2,2,4,6,6,9,12,12-$^2H_8$] cortisol*368.51)/([2,2,4,6,6,9,12,12-$^2H_8$] cortisone*370.52), where 368.51 and 370.52 are the molar masses of D8 cortisone and D8 cortisol. Percent adipose HSD-1 inhibition was calculated as: $100*(1-(MPF_t/MPF_{baseline})$. The time (t) of the sample was considered to be the midpoint of the collection interval. A higher sensitivity assay for D8 cortisol was used to enable quantitation of adipose HSD-1 inhibition of >95%.

Figure 14:
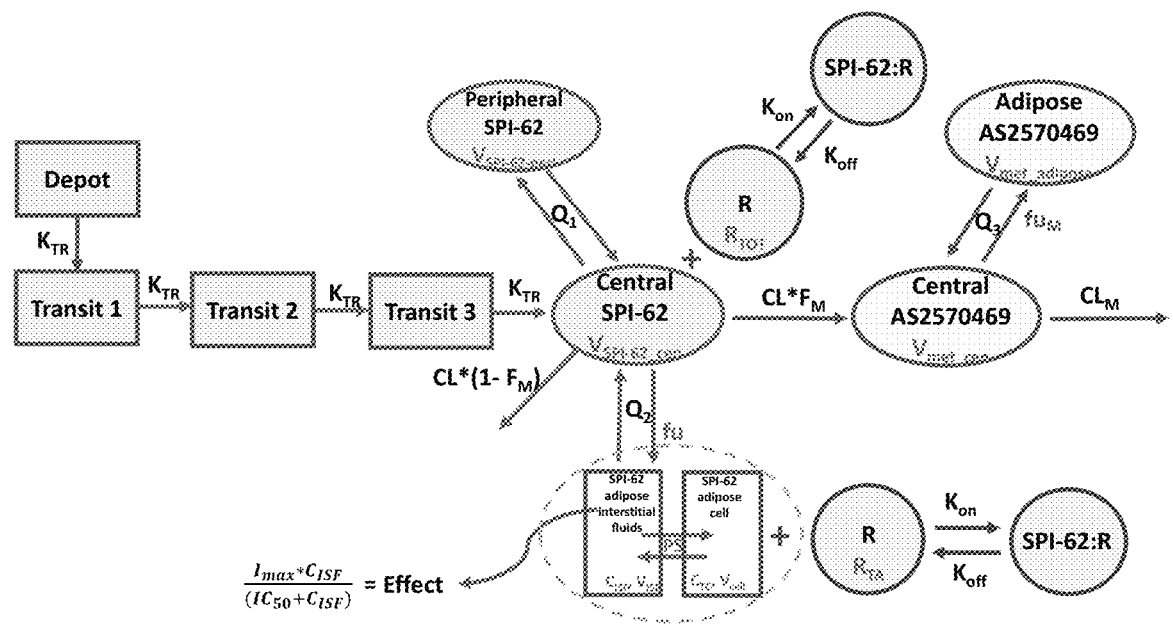
FIG. 14—Shows a target-mediated drug disposition (TMDD) pharmacokinetics-pharmacodynamics (PK/PD) model for SPI-62, including inhibition of adipose HSD-1 as the Effect. AS2570469 is a major metabolite of SPI-62, formed by conversion of the amide to a carboxylic acid.
Figure 14:
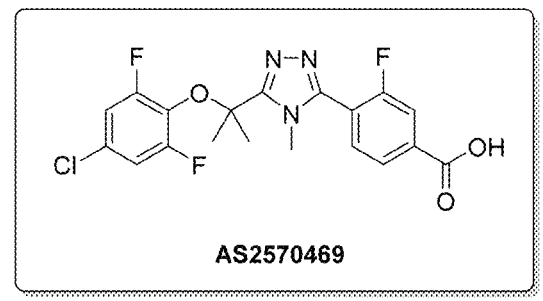

As shown in FIG. 14, data were fit to a target-mediated drug disposition (TMDD) model in which after SPI-62 arrives in the central compartment ($C_p$, $V_{central}$) with a first-order absorption rate constant ($K_a$), it can distribute to the peripheral compartment ($C_t$, $V_{peripheral}$) by the distribution clearance (Q), be eliminated from the system (CL) or bind to the target site (R) with a second-order association rate constant ($k_{on}$) to form a SPI-62-R complex. This complex will dissociate back to free drug and free target with a first-order dissociation rate constant ($k_{off}$). In addition, three sequential and equal first-order transition rate constants ($K_{TR}$) were used to characterize the movement of SPI-62 from the absorption site (i.e., depot compartment) to the central compartment. The model further incorporates an adipose interstitial fluid compartment and an adipose tissue cell compartment in which the transport of SPI-62 molecules between the two compartments is determined by its permeability (PS). In addition, a TMDD process occurs at the adipose tissue: the SPI-62 molecules in adipose tissue cell compartment can bind to the target site (i.e., HSD-1 expressed in adipose cell, $R_{TA}$) with a second-order association rate constant ($k_{on}$) to form an SPI-62-R complex. Since SPI-62 concentrations in adipose dialysate were unbound concentrations sampled using microdialysis, fraction of unbound (fu) was incorporated in the model to account for this. Finally, the complete PK/PD model structure contains an inhibitory $I_{max}$ model to link SPI-62 adipose concentrations with adipose HSD-1 activities.

Key parameter estimates from the model include: association rate constant ($k_{on}$) 1.44 nM$^{-1}$h$^{-1}$, dissociation rate constant ($k_{off}$) 0.264 h$^{-1}$, total target amount in the central compartment ($R_{TOT}$) 7840 nM, total target amount in the adipose compartment ($R_{TA}$) 671 nM, adipose free concentration to achieve 50% HSD-1 inhibition (IC$_{50}$) 23.4 pM, and Hill coefficient (γ) 1.42.

The estimated $K_d$ ($k_{off}/k_{on}$) is 183 pM, which is 69-fold lower than the measured $K_i$ 12.6 nM of SPI-62 for human HSD-1 expressed in CHO cells and 29-fold lower than the $K_i$ 5.3 nM of SPI-62 for purified human HSD-1. The estimated IC$_{50}$ is >700-fold lower than the measured IC$_{50}$ of 17 nM of SPI-62 for purified human HSD-1. Both of these differences indicate the unexpectedly high potency of SPI-62 for HSD-1 in human adipose tissue, which is consistent with a lack of adipose tachyphylaxis due to highly potent competitive binding of SPI-62 to HSD-1 v accumulated cortisone (i.e., HSD-1 substrate).

The estimated total target amount ($R_{TOT}+R_{TA}$) corresponds to 3.6 mg of SPI-62, which comports well with the dose range in which nonlinear PK was observed after single SPI-62 doses. The Hill coefficient indicates moderate positive cooperativity of SPI-62 binding to human HSD-1.

Example 9. Potential Advantages of Pseudo-Irreversible HSD-1 Inhibitors

Described herein is a key discovery that SPI-62 does not show tachyphylaxis on adipose HSD-1 inhibition. Such tachyphylaxis has been previously reported for three other HSD-1 inhibitors (AZD4017, AZD8329, BI-135585), and was potentially considered a class effect. BI-187004, identified as a pseudo-irreversible HSD-1 inhibitor based on fast-on slow-off in vitro enzyme kinetics, showed only limited tachyphylaxis on adipose HSD-1 inhibition. SPI-62 is the first HSD-1 inhibitor for which a lack of adipose tachyphylaxis has been demonstrated. A structural model in which SPI-62 and certain other HSD-1 inhibitors form ternary complexes with NADPH in the human HSD-1 active site predicts that members of this genus of pseudo-irreversible HSD-1 inhibitors will not show tachyphylaxis on adipose HSD-1 inhibition. Based on the relative importance of adipose HSD-1 in regulation of cardiometabolic processes that correspond to morbidity of GC excess, pseudo-irreversible inhibitors might be expected to show clinical advantage over other HSD-1 inhibitors on domains such as glycemic and lipid control, and particularly in patients with GC excess. For example, animal model data for BI-187004 has indicated dependence of glucose lowering efficacy on sustained >90% inhibition of adipose HSD-1. Evidence supportive of that contention also comes from SPI-62 which, subject to limitations including different duration of administration in separate clinical trials, is associated with the largest reported effects for an HSD-1 inhibitor on HbA1c, cholesterol, and triglycerides.

Pseudo-irreversible HSD-1 inhibitors might have additional advantages over other HSD-1 inhibitors. For example, with durable pharmacologic effect, pseudo-irreversible HSD-1 inhibitors are more amenable to less than daily dosing including depot formulations and less likely to show decreased efficacy based on imperfect patient compliance. Additionally, HSD-1 in the human body appears to become completely occupied with approximately 3 mg of a potent small molecule inhibitor. Because pseudo-irreversible inhibitors, once bound, distribute only slowly off HSD-1 a low chronic dose is possible. Several pseudo-irreversible HSD-1 inhibitors, such as SPI-62, ABT-384, MK-0736, and MK-0916, have effective dose ranges below 10 mg daily. In contrast other HSD-1 inhibitors, such as S-707106, AZD4017, INCB-13739, and R05093151, require daily doses of 100 mg or more to show efficacy. With higher doses, the probability of certain types of side effects (e.g., hepatotoxicity which has been noted with AZD4017) can become more likely.

In summary, the present disclosure describes the discovery of a genus of HSD-1 inhibitors with certain shared properties that are likely to be clinically advantageous, particularly for patients with GC excess.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

What is claimed is:

1. A method for treating diabetes and lowering intracellular cortisol level in a human patient with diabetes and an elevated level of cortisol, comprising administering to the patient a therapeutically effective amount of a compound, or a pharmaceutically acceptable salt thereof, wherein the compound is:

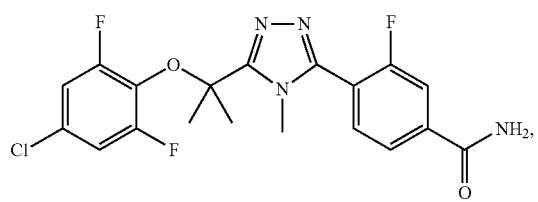 [SMILES: Cn1c(-c2ccc(C(N)=O)cc2F)nnc1C(C)(C)Oc1c(F)cc(Cl)cc1F]

and
wherein the therapeutically effective amount of the compound, or the pharmaceutically acceptable salt thereof, is about 1 mg to about 40 mg daily; wherein the treatment decreases the patient's hemoglobin A1c (HbA1c) levels compared to the patient's HbA1c levels before the compound is initially administered to the patient; and wherein the compound does not show tachyphylaxis for HSD-1 inhibition in human adipose tissue.

2. The method of claim 1, wherein the compound, or the pharmaceutically acceptable salt thereof, is administered to the patient orally, intravenously, intramuscularly, subcutaneously, by inhalation, intranasally, ocularly, or topically.

3. The method of claim 1, wherein the diabetes is type 2 diabetes.

4. The method of claim 1, wherein the therapeutically effective amount of the compound, or the pharmaceutically acceptable salt thereof, is 10 mg or lower daily.

5. The method of claim 1, wherein the therapeutically effective amount of the compound, or the pharmaceutically acceptable salt thereof, is 12 mg daily.

6. The method of claim 1, wherein the compound, or the pharmaceutically acceptable salt thereof, is administered to the patient orally.

7. The method of claim 1, wherein the compound, or the pharmaceutically acceptable salt thereof, is administered to the patient for at least six weeks.

8. The method of claim 1, wherein the compound, or the pharmaceutically acceptable salt thereof, is administered to the patient for at least eight weeks.

9. The method of claim 1, wherein the compound, or the pharmaceutically acceptable salt thereof, is administered to the patient for at least 12 months.

10. The method of claim 1, wherein the patient has a body mass index between 30.0 and 45.0.

11. The method of claim 1, wherein the therapeutically effective amount of the compound, or the pharmaceutically acceptable salt thereof, is about 0.2 mg to about 6 mg daily.

12. The method of claim 1, wherein the therapeutically effective amount of the compound, or the pharmaceutically acceptable salt thereof, is 1 mg, 2 mg, 3 mg, 4 mg, 5 mg, 6 mg, 7 mg, 8 mg, 9 mg, or 10 mg daily.

13. The method of claim 1, wherein the therapeutically effective amount of the compound, or the pharmaceutically acceptable salt thereof, is 11 mg, 12 mg, 13 mg, 14 mg, 15 mg, 16 mg, 17 mg, 18 mg, 19 mg, or 20 mg daily.

14. The method of claim 1, wherein the therapeutically effective amount of the compound, or the pharmaceutically acceptable salt thereof, is 21 mg, 22 mg, 23 mg, 24 mg, 25 mg, 26 mg, 27 mg, 28 mg, 29 mg, or 30 mg daily.

15. The method of claim 1, wherein the therapeutically effective amount of the compound, or the pharmaceutically acceptable salt thereof, is 31 mg, 32 mg, 33 mg, 34 mg, 35 mg, 36 mg, 37 mg, 38 mg, 39 mg, or 40 mg daily.

* * * * *